United States Patent
Yang

(10) Patent No.: US 10,435,720 B2
(45) Date of Patent: *Oct. 8, 2019

(54) RECOMBINANT MICROORGANISM HAVING ENHANCED D(-) 2,3-BUTANEDIOL PRODUCING ABILITY AND METHOD FOR PRODUCING D(-) 2,3-BUTANEDIOL USING THE SAME

(71) Applicant: GS CALTEX CORPORATION, Seoul (KR)

(72) Inventor: Taek-Ho Yang, Daejeon (KR)

(73) Assignee: GS CALTEX CORPORATION, Seoul (KR)

(*) Notice: Subject to any disclaimer, the term of this patent is extended or adjusted under 35 U.S.C. 154(b) by 0 days.

This patent is subject to a terminal disclaimer.

(21) Appl. No.: 15/104,973

(22) PCT Filed: Dec. 16, 2014

(86) PCT No.: PCT/KR2014/012428
§ 371 (c)(1),
(2) Date: Jun. 16, 2016

(87) PCT Pub. No.: WO2015/093831
PCT Pub. Date: Jun. 25, 2015

(65) Prior Publication Data
US 2017/0002384 A1    Jan. 5, 2017

(30) Foreign Application Priority Data
Dec. 16, 2013 (KR) .................. 10-2013-0156802

(51) Int. Cl.
*C12N 1/21* (2006.01)
*C12P 7/18* (2006.01)
*C12N 9/04* (2006.01)
*C12N 15/52* (2006.01)

(52) U.S. Cl.
CPC ............. *C12P 7/18* (2013.01); *C12N 9/0006* (2013.01); *C12N 15/52* (2013.01); *C12Y 101/01004* (2013.01)

(58) Field of Classification Search
None
See application file for complete search history.

(56) References Cited

U.S. PATENT DOCUMENTS

| 2003/0032153 A1 | 2/2003 | Yamamoto et al. | |
| 2013/0330809 A1* | 12/2013 | Mueller | C12N 15/74 435/252.3 |
| 2016/0244730 A1* | 8/2016 | Yang | C12N 9/0006 |

FOREIGN PATENT DOCUMENTS

| CN | 102071174 A | 5/2011 |
| CN | 102071174 B | * 5/2011 |
| CN | 102952826 A | 3/2013 |
| CN | 103361296 A | * 10/2013 |
| CN | 103361296 A | 10/2013 |
| CN | 103740771 A | * 4/2014 |
| WO | 2013076144 A2 | 5/2013 |

OTHER PUBLICATIONS

Siemerink et al., "D-2,3-Butanediol Production Due to Heterologous Expression of an Acetoin Reductase in Clostridium acetobutylicum", Appl. Environ. Microbiol. 77:2582-2588, 2011.*
Zhou et al., Cell Mol Life Sci 63:2260-2290, 2006 (Year: 2006).*
Kozak, M., Gene 234:187-208, 1999 (Year: 1999).*
Celinska et al., Biotechnol. Adv. 27:715-725, 2009 (Year: 2009).*
Guo et al., Biotech. Appl. Biochem. 60:557-563, Nov. 2013 (Year: 2013).*
Kleiner et al., J. Gen. Microbiol. 134:1779-1784, 1988 (Year: 1988).*
Yan et al., Org. Biomol. Chem. 7:3914-3917, 2009 (Year: 2009).*
Qi et al., Biotechnol. Biofuels 7:16, 2014, 12 pages (Year: 2014).*
Park et al., J. Ind. Microbiol. Biotechnol. 42:1419-1425, 2015 (Year: 2015).*
Machine translation of CN 103361296 A, obtained online from Espacenet on Dec. 1, 2017, 11 pages.*
Machine translation of CN 102071174 B, obtained online from Espacenet on Dec. 1, 2017, 14 pages.*
Machine translation of CN 103740771 A, obtained online from Google Patents on Dec. 2, 2017, 6 pages.*
Blomqvist et al., J. Bacteriol. 175:1392-1404, 1993 (Year: 1993).*
Yang et al., J. Biotechnol. 172:59-66, 2014 (Year: 2014).*
Taowei Yang et al., Improved Production of 2,3-Butanediol in Bacillus amyloliquefaciens by Over-Expression of Glyceraldehyde-3-Phosphate Dehydrogenase and 2,3-butanediol Dehydrogenase, Oct. 2, 2013, vol. 8, Issue10, e76149, PLOS ONE, published in San Antonio, USA, 10pages.
Duk-Ki Kim et al., Metabolic engineering of a novel Klebsiella oxytoca strain for enhanced 2,3-butanediol production, Journal of Bioscience and Bioengineering, May 1, 2013, vol. 116 No. 2, published in Daejeon, Republic of Korea, 8 pages.
Zeng et al, Microbial production of diols, Chemical biotechnology, 2011, 8 pages.
International Search Report dated Mar. 6, 2015 corresponding to International Application PCT/KR2014/012428.
Chinese Office Action dated Nov. 1, 2018, in connection with the Chinese Patent Application No. 201480068734.1.

* cited by examiner

*Primary Examiner* — David Steadman
(74) *Attorney, Agent, or Firm* — Hauptman Ham, LLP

(57) ABSTRACT

The present invention relates to a recombinant microorganism for producing D(-) 2,3-butanediol, wherein a gene encoding an enzyme for converting acetoin into D(-) 2,3-butanediol is introduced into a microorganism having a pathway for converting acetoin into 2,3-butanediol. In addition, the present invention relates to a method for producing D(-) 2,3-butanediol by using the recombinant microorganism.

13 Claims, 6 Drawing Sheets
Specification includes a Sequence Listing.

[FIG 1]
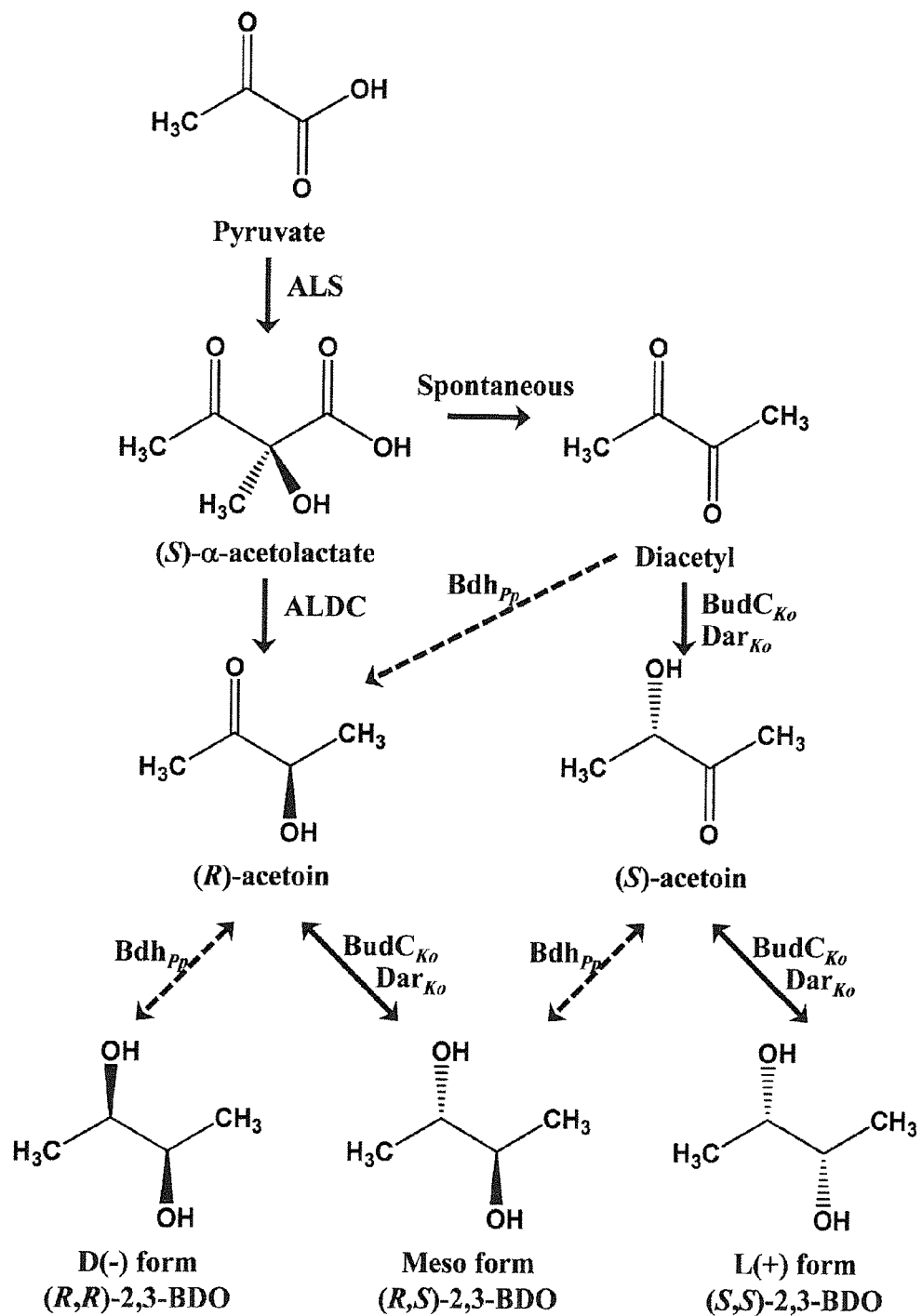

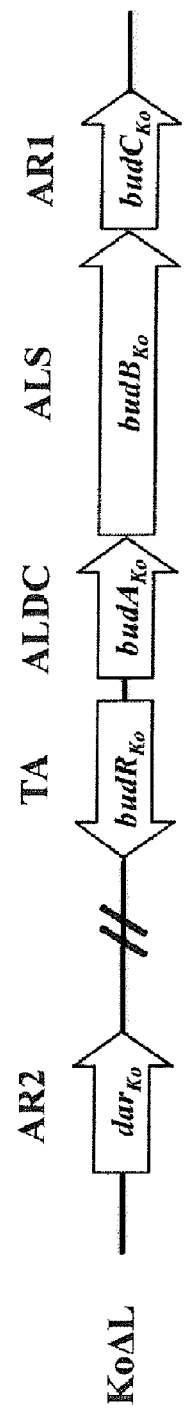
[FIG 2]

[FIG 3]
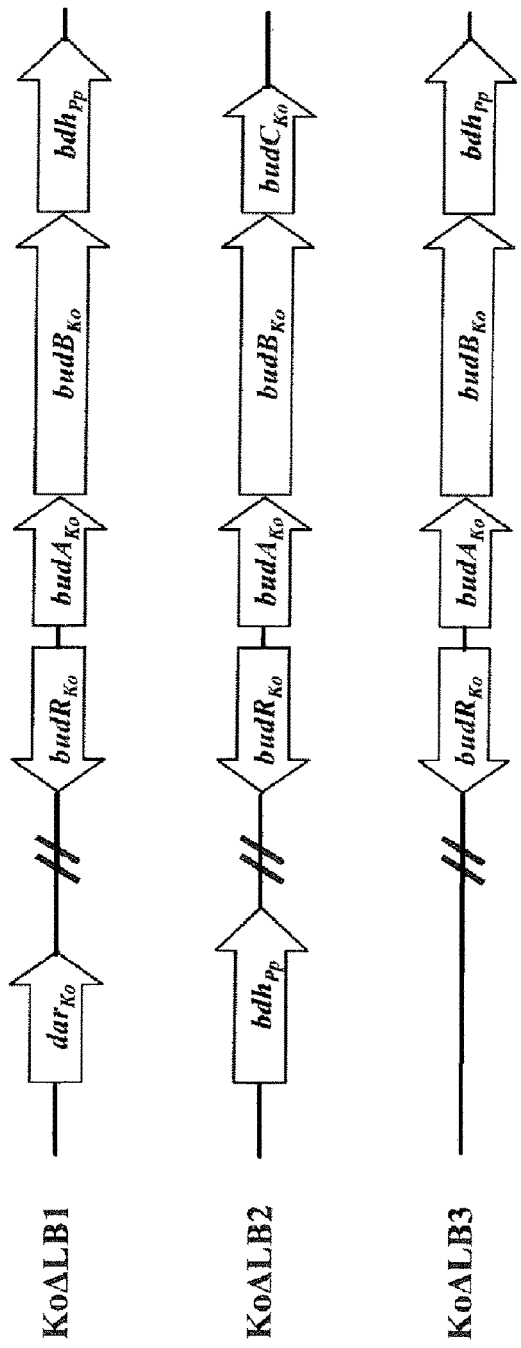

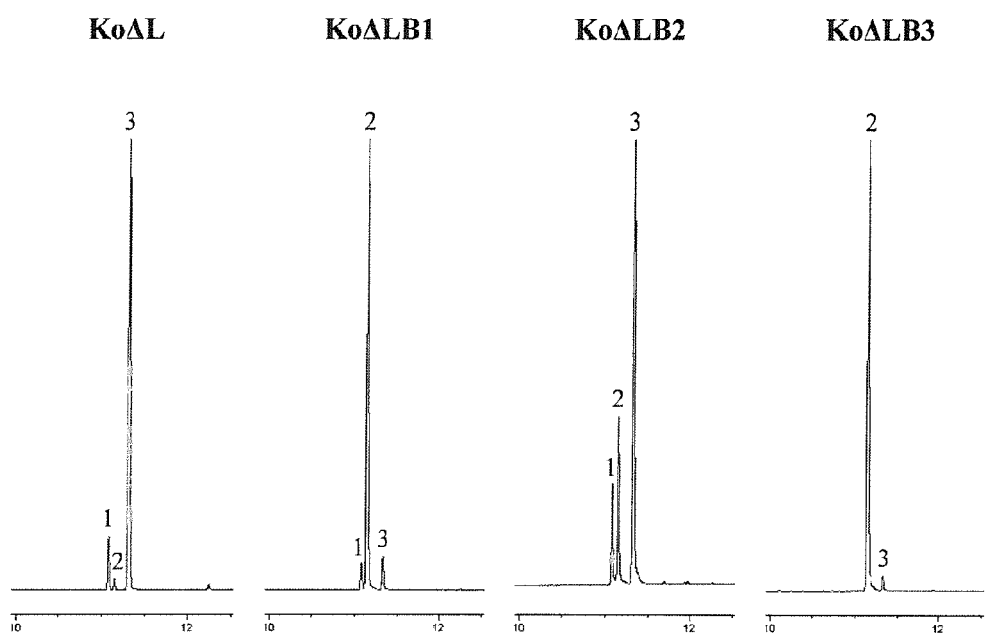
[FIG 4]
1: L(+) 2,3-Butanediol(2S,3S-Butanediol)
2: D(-) 2,3-Butanediol(2R,3R-Butanediol)
3: meso 2,3-Butanediol(2R,3S-Butanediol)

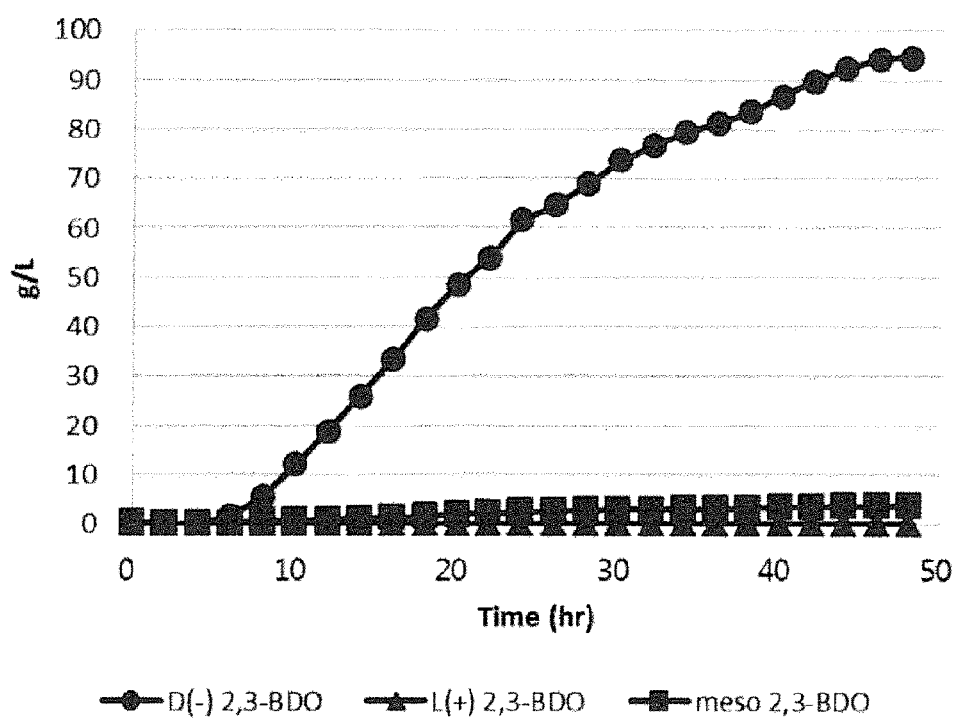

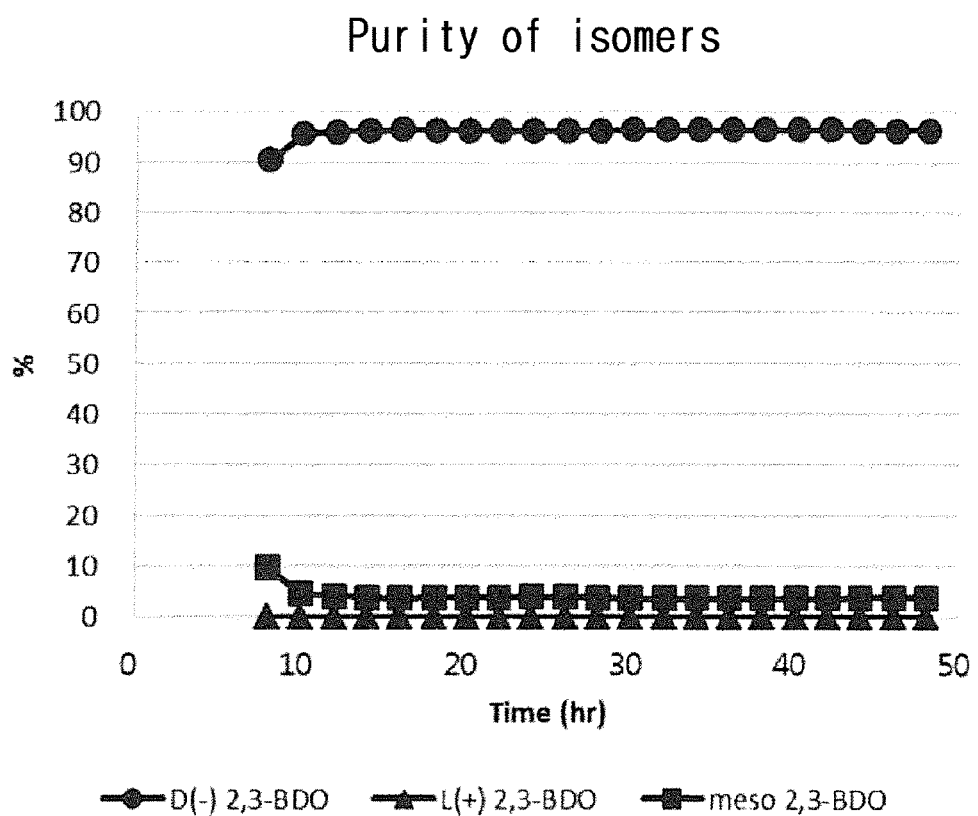
[FIG 6]

RECOMBINANT MICROORGANISM HAVING ENHANCED D(-) 2,3-BUTANEDIOL PRODUCING ABILITY AND METHOD FOR PRODUCING D(-) 2,3-BUTANEDIOL USING THE SAME

CROSS REFERENCE TO RELATED APPLICATION

This application claims the priority of Korean Patent Application No. 10-2013-0156802, filed on Dec. 16, 2013 in the KIPO (Korean Intellectual Property Office). Further, this application is the National Phase application of International Application No. PCT/KR2014/012428 filed Dec. 16, 2014, which designates the United States and was published in Korean.

TECHNICAL FIELD

The present invention relates to a recombinant microorganism having an enhanced ability to produce D(-) 2,3-butanediol and a method for producing D(-) 2,3-butanediol using the same.

BACKGROUND ART 2,3-butanediol is an alcohol (represented by $CH_3CHOHCHOHCH_3$) having four carbons and two hydroxyl (—OH) groups and can be chemically and catalytically converted into 1,3-butadiene, which is a raw material for preparation of synthetic rubbers, and methyl ethyl ketone (MEK), which is a fuel additive and a solvent. 2,3-butanediol is a very important industrial intermediate since 2,3-butanediol can be used as an octane booster through mixing with gasoline.

2,3-butanediol can be produced by chemical synthesis and microbial fermentation. However, due to high production costs, 2,3-butanediol has not been produced on a commercially viable scale. In recent years, with rapid development of techniques for producing 2,3-butanediol through microbial fermentation, fossil fuel price increase and tightened international regulations on environmental contamination, there has been a growing focus on the importance of finding biological methods for producing 2,3-butanediol through microbial fermentation.

Since 2,3-butanediol includes two stereocenters, 2,3-butanediol can be found in three stereoisomers, namely, a D(-) form (levo form, 2R,3R-BDO), an L(+) form (dextro form, 2S,3S-BDO), and a meso form (2R,3S-BDO). 2,3-butanediol having optical activity together with the aforementioned general applicability of 2,3-butanediol can have special applications. For example, D(-) 2,3-butanediol can be used as an anti-freeze agent since it has a very low freezing point. Further, D(-) 2,3-butanediol can be used as an intermediate for medicines and agricultural compounds. However, production of optically pure D(-) 2,3-butanediol through chemical synthesis is not preferred because synthesis and separation/purification thereof are costly. Production of optically pure D(-) 2,3-butanediol through microbial fermentation is economically advantageous (Zeng et al., Curr. Opin. Biotechnol., 22:6, 2011).

Bio-based production of 2,3-butanediol can be made by a great variety of microorganisms through microbial fermentation and representative examples of such microorganisms include microorganisms belonging to genus *Enterobacter*, genus *Klebsiella*, genus *Bacillus*, genus *Serratia*, and the like. Naturally occurring wild type microorganisms have drawbacks in that they mainly produce meso-2,3-butanediol having no optical activity, or even if they could produce 2,3-butanediol isomers having optical activity, the isomers are produced in the form of a mixture.

*Paenibacillus polymyxa* can produce D(-) 2,3-butanediol with high purity. However, *Paenibacillus polymyxa* requires expensive nutrient components and has low productivity and yield, and thus has a problem in that it cannot be directly applied to the current industrialized processes.

As a result of earnest investigation aimed at developing a recombinant microorganism having optical activity allowing it to be used in industrialized processes and capable of producing D(-) 2,3-butanediol, the present inventors identified that a recombinant microorganism in which a specific gene is deleted/substituted produces high purity D(-) 2,3-butanediol with high productivity and yield. Based on this finding, the present invention has been completed.

DISCLOSURE

Technical Problem

It is an object of the present invention to provide a recombinant microorganism having an enhanced ability to produce D(-) 2,3-butanediol and a method for producing D(-) 2,3-butanediol using the same.

Technical Solution

In accordance with one aspect of the present invention, there is provided a recombinant microorganism for producing D(-) 2,3-butanediol,
wherein a gene encoding an enzyme for converting acetoin into D(-) 2,3-butanediol is introduced into a microorganism having a pathway for converting acetoin into 2,3-butanediol.

In accordance with another aspect of the present invention, there is provided a method for producing D(-) 2,3-butanediol, including:
inoculating a culture medium with the recombinant microorganism according to the present invention; and
culturing the recombinant microorganism.

Advantageous Effects

A recombinant microorganism according to the present invention has an enhanced ability to produce D(-) 2,3-butanediol and can regulate ratios of isomers in the produced 2,3-butanediol by regulating a gene to be introduced and a gene to be suppressed.

DESCRIPTION OF DRAWINGS

FIG. 1 shows a biosynthetic pathway of each 2,3-butanediol isomer in 2,3-butanediol producing strains.

FIG. 2 shows an operon of a 2,3-butanediol synthesis related gene in *Klebsiella oxytoca* as a base strain.

FIG. 3 shows an operon of a 2,3-butanediol synthesis related gene in recombinant *Klebsiella oxytoca*.

FIG. 4 show gas chromatography (GC) analysis results of each 2,3-butanediol isomer produced by batch fermentation of recombinant strains of *Klebsiella*.

FIG. 5 shows production results of each 2,3-butanediol isomer upon fed-batch fermentation of a recombinant strain of *Klebsiella* (KoΔLB3).

FIG. 6 shows purity of each 2,3-butanediol isomer upon fed-batch fermentation of a recombinant strain of *Klebsiella* (KoΔLB3).

BEST MODE

The present invention relates to a recombinant microorganism for producing D(−) 2,3-butanediol, wherein a gene encoding an enzyme for converting acetoin into D(−) 2,3-butanediol is introduced into a microorganism having a pathway for converting acetoin into 2,3-butanediol.

In addition, the present invention relates to a method for producing D(−) 2,3-butanediol, including:

inoculating a culture medium with the recombinant microorganism according to the present invention; and culturing the recombinant microorganism.

Hereinafter, the present invention will be described in detail.

Recombinant Microorganism According to the Present Invention

The recombinant microorganism according to the present invention is a recombinant microorganism for producing D(−) 2,3-butanediol, wherein a gene encoding an enzyme for converting acetoin into D(−) 2,3-butanediol is introduced into a microorganism having a pathway for converting acetoin into 2,3-butanediol.

In the recombinant microorganism, at least one gene encoding an enzyme for converting acetoin into meso-2,3-butanediol may be suppressed.

In the recombinant microorganism, a pathway for converting pyruvate into lactate may be suppressed.

Preferably, in the recombinant microorganism according to the present invention, a gene encoding an enzyme for converting acetoin into meso-2,3-butanediol is substituted with a gene encoding an enzyme for converting acetoin into D(−) 2,3-butanediol. More preferably, in the recombinant microorganism according to the present invention, a gene encoding an enzyme for converting acetoin into meso-2,3-butanediol (namely, an enzyme converting (R)-acetoin into meso-2,3-butanediol) is substituted with a gene encoding an enzyme for converting acetoin into D(−) 2,3-butanediol (namely, an enzyme converting (R)-acetoin into D(−) 2,3-butanediol), and a pathway for converting pyruvate into lactate is suppressed.

The microorganism having a pathway for converting acetoin into 2,3-butanediol may be wild type microorganisms or recombinant microorganisms, and examples of such microorganisms may include microorganisms belonging to genus *Enterobacter*, genus *Klebsiella*, genus *Bacillus*, genus *Serratia*, and the like. The microorganism is preferably a microorganism belonging to genus *Klebsiella*, more preferably *Klebsiella oxytoca*.

Preferably, the recombinant microorganism according to the present invention can produce high purity D(−) 2,3-butanediol having higher utility while maintaining 2,3-butanediol production properties of the existing strain of *Klebsiella oxytoca*, namely, strain stability, productivity, production concentration, production yield, and the like by deleting genes encoding AR1 (BudC$_{Ko}$) and/or AR2(Dar$_{Ko}$) enzymes which are 2,3-butanediol conversion enzymes (acetoin reductases) in wild type *Klebsiella oxytoca* and inserting a gene encoding an enzyme having a high activity of converting acetoin into D(−) 2,3-butanediol.

Introduction of Gene Encoding Enzyme for Converting Acetoin into D(−) 2,3-Butanediol The gene encoding an enzyme for converting acetoin into D(−) 2,3-butanediol may be bdh$_{Pp}$, a gene including a nucleotide sequence set forth in SEQ ID NO: 21 or a gene having an identity of 90% or more with the nucleotide sequence set forth in SEQ ID NO: 21, a gene encoding a protein having an amino acid sequence set forth in SEQ ID NO: 20, a gene encoding a protein having an amino acid sequence with 90% or more identity with the amino acid sequence set forth in SEQ ID NO: 20, a gene encoding a BdhPp protein, or a gene encoding a protein having enzyme activity with 90% or more identity with the BdhPp protein, and the like.

Introduction of the genes may be performed through replacement with a specific gene on a genome of a subject strain or insertion into a specific position on a genome of a subject strain. For example, those skilled in the art can newly introduce the activity of proteins by selecting an appropriate method, such as replacing a gene to be deleted on the genome of a subject strain, for instance, budC$_{Ko}$ or dar$_{Ko}$, or genes having an identity of 90% or more with those genes, and the like with the gene encoding the proteins, namely, bdh$_{Pp}$, the gene set forth in SEQ ID NO: 21, or genes having an identity of 90% or more with those genes, and the like, or inserting the gene encoding the proteins, namely, the bdh$_{Pp}$ gene, the gene set forth in SEQ ID NO: 21, or the genes having an identity of 90% or more with those genes, and the like into a new specific position on the genome capable of expressing the genes.

Suppression of Gene Encoding Enzyme for Converting Acetoin into Meso-2,3-Butanediol In the recombinant microorganism according to the present invention, at least one gene encoding an enzyme for converting acetoin into meso-2,3-butanediol may be suppressed. Examples of the genes may include budC$_{Ko}$, dar$_{Ko}$, a gene having a nucleotide sequence set forth in SEQ ID NO: 10 or SEQ ID NO: 12, or a gene having an identity of 90% or more with the nucleotide sequence set forth in SEQ ID NO: 10 or SEQ ID NO: 12, a gene encoding a protein having an amino acid sequence set forth in SEQ ID NO: 9 or SEQ ID NO: 11, or a gene encoding a protein having an amino acid sequence with 90% or more identity with the amino acid sequence set forth in SEQ ID NO: 9 or SEQ ID NO: 11, a gene encoding AR1 protein or AR2 protein, and the like.

Suppression of the genes may include not only suppression of the genes themselves but also activity suppression of proteins encoded by the genes. The activity inhibition of proteins may be performed by expression inhibition of the proteins, enzyme activity inhibition, and the like. For example, those skilled in the art can suppress the gene encoding an enzyme for converting acetoin into meso-2,3-butanediol by selecting suitable methods, such as deleting a gene that encodes the gene or causing mutations in the gene (mutations such as suppression of normal gene expression through modifying, substituting or deleting a partial nucleotide sequence or introducing a partial nucleotide sequence), regulating gene expression during transcription or translation, and the like.

If the gene encoding an enzyme for converting acetoin into meso-2,3-butanediol is not suppressed and the gene encoding an enzyme for converting acetoin into D(−) 2,3-butanediol is introduced, both meso-2,3-butanediol and D(−) 2,3-butanediol are produced in a considerable ratio.

Therefore, it is possible to produce 2,3-butanediol including both meso-2,3-butanediol and D(−) 2,3-butanediol in a considerable ratio.

If the gene encoding an enzyme for converting acetoin into meso-2,3-butanediol is substituted with the gene encoding an enzyme for converting acetoin into D(−) 2,3-butanediol, the gene encoding an enzyme for converting acetoin into meso-2,3-butanediol is suppressed simultaneously with introduction of the gene encoding an enzyme for converting acetoin into D(−) 2,3-butanediol, thereby exhibiting a preferable effect in terms of enhancing the ability to produce D(−) 2,3-butanediol.

Suppression of Pathway for Converting Pyruvate into Lactate

The recombinant microorganism according to the present invention may further suppress a pathway of converting pyruvate into lactate. Lactate dehydrogenase regulates conversion of pyruvate into lactate. The pathway of converting pyruvate to lactate may be suppressed by suppressing lactate dehydrogenase. Suppression of lactate dehydrogenase may be performed by inhibition of gene expression of lactate dehydrogenase, inhibition of enzyme activity of lactate dehydrogenase, and the like. For example, those skilled in the art can suppress lactate dehydrogenase by selecting suitable methods, such as deleting a gene that encodes lactate dehydrogenase, for instance, ldhA, causing mutations in the gene (mutations such as suppression of normal gene expression through modifying, substituting or deleting a partial nucleotide sequence or introducing a partial nucleotide sequence), regulating gene expression during transcription or translation, and the like.

Biological Production of D(−) 2,3-Butanediol Using the Recombinant Microorganism According to the Present Invention The recombinant microorganism according to the present invention has a pathway for biosynthesizing (R)-acetoin as shown in FIG. 1. In the recombinant microorganism according to the present invention, by additionally introducing a gene encoding an enzyme converting (R)-acetoin into D(−) 2,3-butanediol, a pathway for converting (R)-acetoin into D(−) 2,3-butanediol is newly created, and the existing pathway for converting (R)-acetoin into meso-2,3-butanediol is suppressed.

In the present invention, the microorganisms producing 2,3-butanediol may include a series of converting enzymes such as α-acetolactate synthase (ALS), α-acetolactate dicarboxylase (ALDC), and acetoin reductase (AR), as shown in FIG. 1. An operon of a 2,3-butanediol synthesis related gene is depicted in FIG. 2. On the other hand, in a wild type strain of *Klebsiella oxytoca*, pyruvate is converted by acetolactate synthase into α-acetolactate, α-acetolactate is converted by α-acetolactate dicarboxylase into (R)-acetoin, and (R)-acetoin is converted by acetoin reductase into meso-2,3-butanediol, as shown in pathway 1. Both AR1 (BudCKo) and AR2 (DarKo) mentioned above are involved in interconversion between (R)-acetoin and meso-2,3-butanediol.

<Pathway 1>

Pyruvate→α-Acetolactate→(R)-Acetoin→Meso-2,3-Butanediol

In the present invention, D(−) 2,3-butanediol can be produced by newly introducing an enzyme catalyzing the reaction shown in pathway 2, and the enzyme belongs to the acetoin reductase family, which has a site specificity different from that of the existing acetoin reductases, i.e., AR1 (BudCKo) and AR2 (DarKo).

<Pathway 2>

(R)-acetoin→D(−) 2,3-butanediol (levo form, 2R,3R-butanediol)

Method for Producing D(−) 2,3-Butanediol

The present invention relates to a method for producing D(−) 2,3-butanediol, including: inoculating a culture medium with a recombinant microorganism according to the present invention; and culturing the recombinant microorganism. The method for producing D(−) 2,3-butanediol may further include harvesting the produced D(−) 2,3-butanediol.

Method for Producing 2,3-Butanediol

The present invention relates to a method for producing 2,3-butanediol having desired component ratio of 2,3-butanediol isomers using the recombinant microorganism according to the present invention. Namely, if the gene encoding an enzyme for converting acetoin into meso-2,3-butanediol is not suppressed and the gene encoding an enzyme for converting acetoin into D(−) 2,3-butanediol is introduced, 2,3-butanediol including both meso-2,3-butanediol and D(−) 2,3-butanediol in a considerable ratio is produced. In addition, in the case when AR1 is suppressed and the gene encoding an enzyme for converting acetoin into D(−) 2,3-butanediol is introduced and in the case when AR2 is suppressed and the gene encoding an enzyme for converting acetoin into D(−) 2,3-butanediol is introduced, the produced amounts of meso-2,3-butanediol and D(−) 2,3-butanediol in the produced 2,3-butanediol may be different. Similarly, if both AR1 and AR2 are suppressed and the gene encoding an enzyme for converting acetoin into D(−) 2,3-butanediol is introduced, the produced amount of meso-2,3-butanediol is extremely reduced and the proportion of D(−) 2,3-butanediol becomes much higher.

Cultivation

The recombinant microorganism according to the present invention may be cultured under aerobic conditions, preferably under microaerobic conditions. For example, the cultivation may be performed by supplying oxygen, namely air, during cultivation. Specifically, the cultivation is performed by stirring, without being limited thereto. The recombinant microorganism according to the present invention may be cultured in a complex medium, and sorts of the complex medium are not particularly limited. It is obvious that those skilled in the art could appropriately select commonly used and commercially available complex media as desired.

MODE FOR INVENTION

The advantages and features of the present invention and methods for accomplishing the same will become apparent from the following examples. It should be understood that the present invention is not limited to the following examples and may be embodied in different ways, and the following examples are given to provide complete disclosure of the present invention and to provide a thorough understanding of the present invention to those skilled in the art. The present invention should be defined only by the accompanying claims and equivalents thereof <Materials and Methods>

Preparation of Strain of *Klebsiella oxytoca* KCTC 12133BP ΔldhA (KO ΔL)

A strain of lactate dehydrogenase gene (LdhA) deleted *Klebsiella oxytoca* KCTC 12133BP ΔldhA (KO ΔL) was constructed as follows. Firstly, in order to clone a lactate dehydrogenase gene of *Klebsiella oxytoca*, a homologous region 1 (SEQ ID NO: 2) of a target gene ldhA (SEQ ID NO: 1) was amplified using primers of SEQ ID NOs: 3 and 4 by polymerase chain reaction (PCR). Further, a homologous region 2 (SEQ ID NO: 5) was amplified using primers of SEQ ID NOs: 6 and 7 by PCR. Next, the homologous regions 1 and 2 were amplified using the same as templates for PCR, thereby obtaining a completed DNA fragment (SEQ ID NO: 8) in which the homologous regions 1 and 2 were ligated. The completed DNA fragment may include antibiotic resistance genes and the like in order to enhance the probability of recombination of target genes. Further, the completed DNA fragment may include a sacB gene encoding levansucrase in order to remove antibiotic resistance genes recombined in the chromosomes (Table 1).

The prepared DNA fragment was transferred to wild type *Klebsiella oxytoca* through electroporation (25 µF, 200 Ω, 18 kV/cm), in which the target gene was deleted by a homologous recombination mechanism indigenous to the microorganism.

TABLE 1

| SEQ ID NO | Sequence |
|---|---|
| 1 | ATGAAAATCGCTGTGTATAGTACAAAACAGTACGACAAGAAGTAT CTGCAGCATGTTAATGATGCATATGGCTTTGAACTGGAGTTTTTT GACTTCCTGCTAACCGAAAAAACCGCCAAAACCGCCAACGGCTGT GAAGCGGTGTGTATCTTCGTAAACGATGACGGTAGCCGCCCGGTA CTTGAAGAACTGAAAGCCCACGGCGTGCAGTACATCGCGCTGCGC TGCCGCGGGGTTCAACAACGTTGACCTCGATGCCGCCAAAGAGCTG GGCCTGCGGGTGGTGCGGTCCCGGCCTACTCGCCGGAAGCGGTC GCTGAGCACGCGATCGGCATGATGATGTCGCTGAACCGCCGCATT CACCGTGCCTATCAGCGCACCCGCGACGCGAACTTCTCTCTGGAA GGGCTGACCGGTTTCACCATGCACGGTAAAACCGCCGGCGTTATT GGCACCGGTAAAATCGGCGTCGCCGCGCTGCGCATTCTTAAAGGC TTCGGTATGCGTCTGCTGGCGTTTGATCCCTACCCAAGCGCCGCC GCGCTGGATATGGGCGTGGAGTATGTCGATCTTGAAACCCTGTAC CGGGAGTCCGATGTTATCTCACTGCACTGCCCACTGACCGATGAA AACTACCATTTGCTGAACCATGCCGCGTTCGATCGCATGAAAGAC GGGGTGATGATCATCAACACCAGCCGCGGCGCGCTCATCGATTCG CAGGCAGCGATCGACGCCCTGAAGCATCAGAAAATTGGCGCGCTG GGGATGGACGTGTATGAGAACGAACGCGATCTGTTCTTTGAAGAT AAGTCTAATGACGTGATTCAGGATGATGTGTTCCGCCGTCTCTCC GCCTGCCATAACGTCCTGTTTACCGGTCACCAGGCGTTTCTGACC GCGGAAGCGTTGATCAGCATTTCGCAAACCACCCTCGACAACCTG CGTCAAGTGGATGCAGGCGAAACCTGTCCTAACGCACTGGTCTGA |
| 2 | ATGACGTTCGCTAAATCCTGCGCCGTCATCTCGCTGCTGATCCCG GGCACCTCCGGGCTACTGCTGTTCGGCACCCTGGCATCGGCCAGC CCGGGACATTTCCTGTTAATGTGGATGAGCGCCAGCCTCGGCGCT ATCGGCGGATTCTGGCTCTCGTGGCTGACGGGCTACCGCTACCGG TACCATCTGCATCGTATCCGCTGGCTTAATGCCGAACGCCTCGCT CGCGGCCAGTTGTTCCTGCGCCGCCACGGCGCGTGGGCAGTCTTT TTTAGCCGCTTTCTCTCTCCGCTTCGCGCCACCGTGCCGCTGGTA ACCGGCGCCAGCGGCACCTCTCTCTGGCAGTTTCAGCTCGCCAAC GTCAGCTCCGGGCTGCTCTGGCCGCTGATCCTGCTGGCGCCAGGC GCGTTAAGCCTCAGCTTTTGATGAAAGGTATTGTCTTTTAAAGAG ATTTCTTAACACCGCGATATGCTCTAGAATTATTACTATAACCTG CTGATTAAACTAGTTTTTAACATTTGTAAGATTATTTTAATTATG CTACCGTGACGGTATTATCACTGGAGAAAAGTCTTTTTTCCTTGC CCTTTTGTGC |
| 3 | Ko_ldhA_FP1-CACGGATCCATGACGTTCGCTAAATCCTGC |
| 4 | Ko_ldhA_RP1-GCACAAAAGGGCAAGGAAAAAAGACTTTTCTCC AGTGATA |
| 5 | TATCACTGGAGAAAAGTCTTTTTTCCTTGCCCTTTTGTGCTCCCC CTTCGCGGGGGGCACATTCAGATAATCCCCACAGAAATTGCCTGC GATAAAGTTACAATCCCTTCATTTATTAATACGATAAATATTTAT TGTCGACCAGAGCGGAACAGCTTCAGCACCACCGTTTTGTGCTGA CCAGCGTTAGGAGATTAAATGAACAAGTATGCTGCGCTGCTGGCG GTGGGAATGTTGCTATCGGGCTGCGTTTATAACAGCAAGGACGGG CAGCCGCTGAATGCCGCGGATAAGCCGCAGGAGCTGAGCTTCGGC GAAAAGATGCCCATTACGGGCAAGATGTCTGTTTCAGGTAATATG TGCAACCGCTTCAGCGGCACGGGCAAAGTCTCTGAACGCGAGCTG AAGGTTGAAGAGCTGGCAATGACCCGCATGCTCTGCACGGACTCG CAGCTTAACGCCCTGGACGCCACGCTGAGCAAAATGCTGCGCGAA GGCGCGCAGGTCGACCTGACGGAAACGCAGCTAACGCTGGCGACC GCCGACCAGACGCTGGTGTATAAGCTCGCCGACCTGATGAATTAA TAATTA |
| 6 | Ko_ldhA_FP2-TATCACTGGAGAAAAGTCTTTTTTCCTTGCCCT TTTGTGC |
| 7 | Ko_ldhA_RP2-CCTGCGGCCGCTAATTATTAATTCATCAGGTC |
| 8 | ATGACGTTCGCTAAATCCTGCGCCGTCATCTCGCTGCTGATCCCG GGCACCTCCGGGCTACTGCTGTTCGGCACCCTGGCATCGGCCAGC CCGGGACATTTCCTGTTAATGTGGATGAGCGCCAGCCTCGGCGCT ATCGGCGGATTCTGGCTCTCGTGGCTGACGGGCTACCGCTACCGG TACCATCTGCATCGTATCCGCTGGCTTAATGCCGAACGCCTCGCT CGCGGCCAGTTGTTCCTGCGCCGCCACGGCGCGTGGGCAGTCTTT TTTAGCCGCTTTCTCTCTCCGCTTCGCGCCACCGTGCCGCTGGTA ACCGGCGCCAGCGGCACCTCTCTCTGGCAGTTTCAGCTCGCCAAC GTCAGCTCCGGGCTGCTCTGGCCGCTGATCCTGCTGGCGCCAGGC GCGTTAAGCCTCAGCTTTTGATGAAAGGTATTGTCTTTTAAAGAG ATTTCTTAACACCGCGATATGCTCTAGAATTATTACTATAACCTG CTGATTAAACTAGTTTTTAACATTTGTAAGATTATTTTAATTATG CTACCGTGACGGTATTATCACTGGAGAAAAGTCTTTTTTCCTTGC CCTTTTGTGCTCCCCCTTCGCGGGGGGCACATTCAGATAATCCCC ACAGAAATTGCCTGCGATAAAGTTACAATCCCTTCATTTATTAAT ACGATAAATATTTATTGGAGAAAATTTCAAGAAGTATGCTGCGCTG CTGGCGGTGGGAATGTTGCTATCGGGCTGCGTTTATAACAGCAAG GTGTCGACCAGAGCGGAACAGCTTCAGCACCACCGTTTTGTGCTG ACCAGCGTTAACGGGCAGCCGCTGAATGCCGCGGATAAGCCGCAG GAGCTGAGCTTCGGCGAAAAGATGCCCATTACGGGCAAGATGTCT GTTTCAGGTAATATGTGCAACCGCTTCAGCGGCACGGGCAAAGTC TCTGACGGCGAGCTGAAGGTTGAAGAGCTGGCAATGACCCGCATG CTCTGCACGGACTCGCAGCTTAACGCCCTGGACGCCACGCTGAGC AAAATGCTGCGCGAAGGCGCGCAGGTCGACCTGACGGAAACGCAG CTAACGCTGGCGACCGCCGACCAGACGCTGGTGTATAAGCTCGCC GACCTGATGAATTAATAATTA |

Identification of 2,3-Butanediol Conversion Enzyme and Genes Thereof

Enzymes related to 2,3-butanediol synthesis and consumption pathways were screened using KEGG database and NCBI database based on genome information of *Klebsiella oxytoca* KCTC 12133BP. As a result, it was confirmed that all species belonging to *Klebsiella oxytoca*, genome information of which is known, have at least two 2,3-butanediol conversion enzymes (AR1 and AR2).

The amino acid sequence of AR1 is set forth in SEQ ID NO: 9, and the nucleotide sequence of $budC_{Ko}$ which encodes AR1 is set forth in SEQ ID NO: 10. Meanwhile, the amino acid sequence of AR2 is set forth in SEQ ID NO: 11, and the nucleotide sequence of $dar_{Ko}$ which encodes AR2 is set forth in SEQ ID NO: 12 (Table 2).

TABLE 2

| SEQ ID NO | Sequence |
|---|---|
| 9 | MKKVALVTGAGQGIGKAIALRLVKDGFAVAIADYNDATAQAVADEI NRSGGRALAVKVDVSQRDQVFAAVEQARKGLGGFDVIVNNAGVAPS TPIEEIREEVIDKVYNINVKGVIWGIQAAVEAFKKEGHGGKIINAC SQAGHVGNPELAVYSSSKFAVRGLTQTAARDLAHLGITVNGYCPGI VKTPMWAEIDRQVSEAAGKPLGYGTQEFAKRITLGRLSEPEDVAAC VSYLAGPDSNYMTGQSLLIDGGMVFN |
| 10 | ATGAAAAAAGTCGCACTCGTCACCGGCGCGGGCCAGGGTATCGGTA AAGCTATCGCCCTTCGTCTGGTAAAGATGGTTTTGCCGTGGCTAT CGCCGATTATAACGACGCCACCGCGCAGGCGGTCGCTGATGAAATT AACCGCAGCGGCGGCCGGGCGCTAGCGGTGAAGGTGGATGTGTCTC AACGCGATCAGGTTTTTGCCGCCGTCGAACAGGCGCGCAAGGGTCT CGGCGGTTTTGACGTGATCGTCAACAACGCCGGGGTTGCGCCCTCC ACACCAATCGAAGAGATTCGCGAGGAGGTGATCGATAAAGTCTACA ATATCAACGTTAAAGGCGTTATCTGGGGCATCCAGGCCGCGGTAGA GGCGTTTAAAAAAGAGGGCCACGGCGGCAAAATTATCAACGCCTGC TCCCAGGCGGGCCATGTAGGTAACCCGGAGCTGGCGGTCTATAGCT |

TABLE 2-continued

| SEQ ID NO | Sequence |
|---|---|
| | CCAGTAAATTTGCCGTGCGCGGCCTGACGCAAACCGCCGCCCGCGA TCTGGCGCATCTGGGGATTACCGTAAACGGCTACTGCCCGGGGATC GTCAAAACCCCAATGTGGGCGGAAATTGACCGCCAGGTTTCCGAAG CGGCGGGTAAACCGCTGGGCTACGGAACCCAGGAGTTCGCCAAACG CATTACCCTTGGGCGGCTATCCGAGCCGGAAGACGTCGCAGCCTGC GTCTCTTATCTCGCCGGTCCGGACTCCAATTATATGACCGGCCAAT CGCTGCTGATCGATGGCGGCATGGTATTTAAC |
| 11 | MAIENKVALVTGAGQGIGRGIALRLAKDGASVMLVDVNPEGIAAVA AEVEALGRKAATFVANIADRAQVYAAIDEAEKQLGGFDIIVNNAGI AQVQALADVTPEEVDRIMRINVQGTLWGIQAAAKKFIDRQQKGKII NACSIAGHDGFALLGVYSATKFAVRALTQAAAKEYASRGITVNAYC PGIVGTGMWTEIDKRFAEITGAPVGETYKKYVEGIALGRAETPDDV ASLVSYLAGPDSDYVTGQSILIDGGIVYR |
| 12 | ATGGCTATCGAAAATAAAGTTGCGCTGGTAACCGGCGCCGGTCAGG GCATTGGCCGCGGTATTGCGTTGCGTCTGGCCAAAGACGGCGCGTC GGTGATGCTGGTCGACGTGAACCCTGAAGGGATTGCCGCCGTCGCC GCCGAAGTGGAAGCGCTGGGACGCAAAGCAGCCACCTTCGTCGCTA ACATCGCCGATCGCGCGCAGGTGTACGCCGCCATTGATGAAGCGGA AAAACAGCTGGGCGGCTTTGATATTATCGTGAACAACGCCGGGATC GCCCAGGTTCAGGCGCTGGCCGATGTGACGCCTGAAGAAGTGGACC GCATCATGCGCATCAACGTTCAGGGTACCCTGTGGGGTATTCAGGC GGCGGCGAAAAAATTCATCGATCGTCAGCAGAAAGGGAAAATCATC AACGCCTGCTCTATCGCCGGTCATGATGGTTTCGCGCTGCTGGGCG TTTATTCCGCCACCAAATTTGCCGTACGCGCCCTGACGCAGGCGGC GGCGAAGGAGTATGCCAGCCGCGGCATTACGGTTAATGCCTACTGT CCGGGGATTGTGGGAACCGGGATGTGGACCGAAATCGATAAGCGCT TTGCGGAAATTACCGGTGCGCCGGTGGGCGAAACTTATAAAAAATA CGTTGAAGGCATCGCCCTTGGCCGCGCCGAAACGCCGGACGATGTG GCAAGCCTGGTCTCTTATCTGGCAGGCCCGGATTCCGATTATGTTA CCGGTCAGTCGATTCTGATCGATGGCGGTATTGTTTACCGT |

Preparation of Strain of *Klebsiella oxytoca* KCTC 12133BP ΔldhA Δdar$_{Ko}$

In order to delete AR2, a homologous region 1 (SEQ ID NO: 13) of a target gene dar$_{Ko}$ (SEQ ID NO: 12) was amplified using primers of SEQ ID NOs: 14 and 15 by PCR. Further, a homologous region 2 (SEQ ID NO: 16) was amplified using primers of SEQ ID NOs: 17 and 18 by PCR. Next, the homologous regions 1 (SEQ ID NO: 13) and 2 (SEQ ID NO: 16) were amplified using the same as templates for PCR, thereby obtaining a completed DNA fragment (SEQ ID NO: 19) in which the homologous regions 1 and 2 were ligated (Table 3).

TABLE 3

| SEQ ID NO | Sequence |
|---|---|
| 13 | GGAGGTCGGCCGGAAGCTCGCCTTGCAGCAGCTGCAGAAACGACGG GCTCCACCCCTGCCACAAGGGCCGCAGCGCCTCCTGCAGATAGCGT ATAAACAGTAGCGGCGCGTTGTCATCCTCTTCAAGGCTCAGCCAGG CCAGCGCATCCCCTTGTCGAAGGCGGTGTCGATACCACTGCGCCAG CAGGGTGGTTTTGCCAAATCCGGCGGGCGCGCGCACCAGGGTTAAA CGGCGGGAGACGGCGGCGTCGAGGCGCTGTAGCAGGCGCTCCCGCG ATAGCAGACTTTCCGGCGTACGGGGCGGCGTAAAGCGCGTGGAGAT AAGCGGCAGCGTCCCCGTGAAGCGTAAAGGTTCCTGATGAACAAGC GCTGCCAGCGCATCATCCGCCGAGGATAAAAAGGCCATACCACGAT TACTCCTTAATCCAGTCCGTACGCTCATTATCCCCCCCATCAGGGG GGTAGGCCACGCTTATCGCGCCCGATAGAGTAGTGCCATTCGCCGC AGCGGCTACGACGACATCGGCCGCGGGCCTCCCTAGTTTATTAATC AGTACAAGGTGAGTACAGACATGGCTATCGAAAATAAAGTTGCGAC CGGTCAGTCGATTCTGATCGATG |
| 14 | TCTAGAGGATCCGGAGGTCGGCCGGAAGCTCGCC |
| 15 | CATCGATCAGAATCGACTGACCGGTCGCAACTTTATTTTCGATAGC CATGTC |

TABLE 3-continued

| SEQ ID NO | Sequence |
|---|---|
| 16 | GACATGGCTATCGAAAATAAAGTTGCGACCGGTCAGTCGATTCTGA TCGATGGCGGTATTGTTTACCGTTAAGGGATAAACCCGGCGCAGAA CGCGCCGGGTTTTTGCGGGGTTACGCGTTAGCCGCGGGCTCCTGCG GCTTGTCGCTACGGGTGTTTTCCAGCATCCGGCGAACCGGAACAAT CAGCAGGCACAGCACCGCGGCGCAGATCAGCAGCGCAATAGAGCAG CGTGCGAACAGGTCGGGCAGCATATCCAGCTGATCGGCCTTCACGT GACCGCCAATCAGACCCGCCGCCAGGTTCCCCAGGGCGCTGGCGCA GAACCACAGCCCCATCATCTGGCCGCGCATTCTTTCCGGCGCCAGC AGCGTCATGGTCGCGAGGCCAATCGGGCTGAGGCACAGCTCGCCCA GCGTCAGCATCAGAATACTGCCCACCAGCCACATCGGCGAGACGCC CGCGCCGTTGTTGCTCAGGACGTTTTGCGCCGCCAGCATCATCAGG CCAAAGCCCGCCGCCGCGCATAAAATACCGATAACAAACTTGGTGA TGCTGCTCGGACGCACGTTTTTACGCGCCAGCGCAGGCCACGCCCA GCTAAATACC |
| 17 | GACATGGCTATCGAAAATAAAGTTGCGACCGGTCAGTCGATTCTGA TCGATG |
| 18 | ATCGCGGCCGCGGTATTTAGCTGGGCGTGGCCTGC |
| 19 | GGAGGTCGGCCGGAAGCTCGCCTTGCAGCAGCTGCAGAAACGACGG GCTCCACCCCTGCCACAAGGGCCGCAGCGCCTCCTGCAGATAGCGT ATAAACAGTAGCGGCGCGTTGTCATCCTCTTCAAGGCTCAGCCAGG CCAGCGCATCCCCTTGTCGAAGGCGGTGTCGATACCACTGCGCCAG CAGGGTGGTTTTGCCAAATCCGGCGGGCGCGCGCACCAGGGTTAAA CGGCGGGAGACGGCGGCGTCGAGGCGCTGTAGCAGGCGCTCCCGCG ATAGCAGACTTTCCGGCGTACGGGGCGGCGTAAAGCGCGTGGAGAT AAGCGGCAGCGTCCCCGTGAAGCGTAAAGGTTCCTGATGAACAAGC GCTGCCAGCGCATCATCCGCCGAGGATAAAAAGGCCATACCACGAT TACTCCTTAATCCAGTCCGTACGCTCATTATCCCCCCCATCAGGGG GGTAGGCCACGCTTATCGCGCCCGATAGAGTAGTGCCATTCGCCGC AGCGGCTACGACGACATCGGCCGCGGGCCTCCCTAGTTTATTAATC AGTACAAGGTGAGTACAGACATGGCTATCGAAAATAAAGTTGCGAC CGGTCAGTCGATTCTGATCGATGGCGGTATTGTTTACCGTTAAGGG ATAAACCCGGCGCAGAACGCGCCGGGTTTTTGCGGGGTTACGCGTT AGCCGCGGGCTCCTGCGGCTTGTCGCTACGGGTGTTTTCCAGCATC CGGCGAACCGGAACAATCAGCAGGCACAGCACCGCGGCGCAGATCA GCAGCGCAATAGAGCAGCGTGCGAACAGGTCGGGCAGCATATCCAG CTGATCGGCCTTCACGTGACCGCCAATCAGACCCGCCGCCAGGTTC CCCAGGGCGCTGGCGCAGAACCACAGCCCCATCATCTGGCCGCGCA TTCTTTCCGGCGCCAGCAGCGTCATGGTCGCGAGGCCAATCGGGCT GAGGCACAGCTCGCCCAGCGTCAGCATCAGAATACTGCCCACCAGC CACATCGGCGAGACGCCCGCGCCGTTGTTGCTCAGGACGTTTTGCG CCGCCAGCATCATCAGGCCAAAGCCCGCCGCCGCGCATAAAATACC GATAACAAACTTGGTGATGCTGCTCGGACGCACGTTTTTACGCGCC AGCGCAGGCCACGCCCAGCTAAATACC |

The previously constructed lactate dehydrogenase gene (LdhA) deleted *Klebsiella oxytoca* KCTC 12133BP ΔldhA (KOΔL) was prepared. The DNA fragment set forth in SEQ ID NO: 19 was transferred to *Klebsiella oxytoca* (KO ΔL) through electroporation (25 μF, 200 Ω, 18 kV/cm). As a result, a recombinant strain of *Klebsiella oxytoca* KCTC 12133BP ΔldhA Δdar$_{Ko}$ in which AR2 (DarKO) was deleted from KO ΔldhA was constructed.

<Experimental Example 1> Preparation of Recombinant Microorganism

Strain of *Klebsiella oxytoca* KCTC 12133BP ΔldhA bud-C$_{Ko}$::Bdh$_{Pp}$ (KoΔLB1)

BdhPp which is a *Paenibacillus polymyxa* derived acetoin reductase is an enzyme belonging to a medium-chain dehydrogenase/reductase family. Recombinant *Klebsiella oxytoca* in which a gene encoding budC$_{Ko}$ as a *Klebsiella oxytoca* KCTC 12133BP innate acetoin reductase was substituted with bdh$_{Pp}$ which encodes Bdh$_{Pp}$ was constructed as follows. Specifically, recombinant *Klebsiella oxytoca* was constructed using *Klebsiella oxytoca* KCTC 12133BP ΔldhA (Ko ΔL) in accordance with the following method. Gene cluster of this strain is depicted in FIG. 3. The amino acid sequence of *Paenibacillus polymyxa* KCTC 1663 originated Bdh$_{Pp}$ is set forth in SEQ ID NO: 20, and a nucleotide sequence of bdh$_{Pp}$ gene that encodes Bdh$_{Pp}$ is set forth in SEQ ID NO: 21 (Table 4).

TABLE 4

| SEQ ID NO | Sequence |
| --- | --- |
| 20 | MQALRWHGVKDLRLENIEQPAALPGKVKIKVEWCGICGSDLHEYV AGPIFIPENAQHPLTGEKAPIVMGHEFSGQVVEIGEGVTKIQVGD RVVVEPVFACGECDACRQGKYNLCDKMGFLGLAGGGGGFSEYVAA DEHMVHKIPESVSFEQGALVEPSAVALYAVRQSQLKVGDKAVVFG AGPIGLLVIEALKASGASEIYAVELSEERKAKAEELGAIVLDPKT YDVVEELHKRTNGGVDVAYEVTGVPPVLTQAIESTKISGQIMIVS IFEKEAPIKPNNIVMKERNLTGIIGYRDVFPAVISLMEKGYFPAD KLVTKRIKLEEVIEQGFEGLLKEKNQVKILVSPKA |
| 21 | ATGCAAGCATTGAGATGGCATGGAGTAAAAGATTTACGTTTGGAA AACATTGAGCAACCCGCTGCTCTTCCAGGAAAAGTAAAAATCAAA GTAGAATGGTGTGGCATTTGCGGAAGTGATCTTCACGAATATGTA GCAGGACCGATCTTCATTCCTGAAAACGCTCAGCATCCACTGACT GGCGAAAAAGCTCCGATTGTGATGGGACATGAATTTTCTGGACAA GTCGTTGAAATCGGTGAAGGTGTAACTAAAATTCAGGTTGGCGAC CGTGTAGTCGTAGAACCGGTTTTTGCATGTGGAGAATGTGATGCA TGTAGACAAGGCAAATATAACCTTTGCGATAAAATGGGCTTCCTC GGTTTTGGCAGGCGGCGGCGGTGGATTTTCTGAATATGTCGCAGCT GACGAGCACATGGTTCACAAAATTCCAGAAAGCGTATCCTTCGAG CAAGGCGCTTTGGTAGAGCCTTCGGCCGTTGCTTTGTACGCTGTA CGTCAAAGCCAACTGAAAGTCGGCGACAAAGCTGTCGTGTTTGGC GCTGGTCCTATCGGATTGCTGGTTATTGAAGCGTTGAAAGCTTCG GGCGCATCTGAGATTTATGCAGTAGAGCTTTCCGAGGAGCGTAAA GCTAAAGCTGAAGAGCTGGGTGCTATTGTGCTTGATCCTAAAACT TATGATGTTGTGGAAGAACTGCACAAACGGACCAACGGTGGCGTA GATGTAGCCTATGAAGTCACTGGAGTACCTCCTGTGCTGACTCAA GCGATTGAATCCACTAAAATTAGCGGACAAATCATGATCGTCGAC ATTTTTGAAAAAGAAGCTCCAATCAAACCGAACAATATCGTTATG AAGGAACGCAATCTGACTGGTATTATCGGCTACCGTGATGTATTC CCGGCTGTCATCAGCTTGATGGAAAAAGGGTATTTCCCTGCTGAC AAGCTTGTGACCAAACGTATTAAGCTCGAAGAAGTAATCGAGCAA GGTTTTGAAGGTCTCCTGAAAGAAAAAAATCAGGTTAAAATCCTG GTATCTCCGAAAGCC |

Firstly, in order to in-frame substitute budC$_{Ko}$ gene (SEQ ID NO: 10) of *Klebsiella oxytoca* KCTC 12133BP innate acetoin reductase with bdh$_{Pp}$ (SEQ ID NO: 21) as a target gene, a homologous region 1 (SEQ ID NO: 22) of budC$_{Ko}$ was amplified by PCR using primers of SEQ ID NOs: 23 and 24. In addition, bdh$_{Pp}$ (SEQ ID NO: 21) was amplified by PCR using primers of SEQ ID NOs: 25 and 26. A homologous region 2 (SEQ ID NO: 27) of budC$_{Ko}$ was amplified by PCR using primers of SEQ ID NOs: 28 and 29. Next, the homologous region 1 (SEQ ID NO: 22), bdh$_{Pp}$ (SEQ ID NO: 21), and the homologous region 2 (SEQ ID NO: 27) were amplified by PCR using those regions as templates for PCR, thereby obtaining a completed DNA fragment (SEQ ID NO: 30) in which the homologous region 1, bdh$_{Pp}$, and the homologous region 2 were ligated (Table 5).

The completed DNA fragment may include antibiotic resistance genes and the like in order to enhance the probability of recombination of target genes. Further, the completed DNA fragment may include a sacB gene encoding levansucrase in order to remove antibiotic resistance genes recombined in the chromosomes.

TABLE 5

| SEQ ID NO | Sequence |
| --- | --- |
| 22 | CCGCATCACCGGCAAAGCGGGCGTCGCGCTGGTCACGTCCGGACC GGGCTGCTCTAACCTGATTACCGGGATGGCAACGGCCAATAGCGA AGGCGACCCGGTGGTGGCGCTGGGCGGCGCGGTAAAACGCGCCGA |

TABLE 5-continued

| SEQ ID NO | Sequence |
| --- | --- |
| | CAAGGCCAAACAGGTGCACCAGAGTATGGATACGGTGACGATGTT TAGCCCGGTGACCAAATACTCGGTGGAAGTCACCGCGCCGGAAGC GCTGGCGGAAGTTGTCTCCAACGCGTTTCGTGCAGCCGAGCAGGG ACGCCCCGGCAGCGCCTTCGTCAGCCTGCCGCAGGACGTGGTCGA CGGGCCGGTCCACGCCAGGGTTCTGCCCGCCGGCGATGCGCCGCA GACCGGCGCGGCGCCGGACGACGCCATTGCGCGAGTCGCGAAGAT GATTGCCGGCGCGAAAAATCCGATATTTCTGCTCGGCCTGATGGC CAGCCAGACGGAAAACAGCGCGGCGCTGCGCGAATTGCTGAAAAA AAGTCATATCCCGGTGACCAGCACCTATCAGGCCGCCGGCGCAGT CAATCAGGATCACTTTTACCCGCTTCGCCGGACGGGTTGGTCTGTT CAACAACCAGGCAGGGGATCGACTCCTGCATCTCGCCGACCTGGT CATCTGCATCGGCTATAGTCCGGTGGAGTACGAGCCGGCCATGTG GAATAACGGTAACGCCACGCTGGTACATATCGACGTGCTGCCCGC TTACGAAGAGCGTAATTATACCCCGGACGTCGAGCTGGTCGGCAA TATCGCCGCCACCCTGAACAAACTGTCTCAACGCATCGACCACCA GCTGGTGCTCTCGCCGCAGGCCGCCGAGATCCTTGTCGACCGCCA GCATCAGCGGGAGCTCCTCGACCGCCGCGGTGCGCACCTGAACCA GTTCGCGCTTCATCCGCTGCGCATCGTTCGCGCCATGCAGGACAT CGTCAATAGCGATGTCACCCTGACCGTCGATATGGGGAGCTTTCA TATCTGGATCGCCCGCTATCTCTACAGCTTTCGCGCCCGTCAGGT CATGATTTCCAACGGTCAACAGACCATGGGCGTGGCGCTGCCGTG GGCGATTGGCGCCTGGCTGGTCAATCCGCAGCGCAAAGTGGTTTC CGTTTCCGGCGACGGCGGTTTCCTGCAGTCCAGCATGGAGCTGGA GACCGCTGTACGGCTGAAAGCGAACGTCCTGCATATCATCTGGGT CGATAACGGCTACAACATGGTGGCGATTCAGGAGGAGAAAAAATA CCAGCGGCTCTCCGGCGTTGAGTTCGGCCCGGTGGATTTTAAAGT CTACGCCGAAGCCTTCGGCGCCAAAGGGTTTGCGGTAGAGAGCGC CGAAGCCCTTGAGCCGACGCTGCGGGCGGCGATGGACGTCGACGG CCCCGCCGTCGTAGCCATCCCCGTGGATTACCGCGATAACCCGCT GCTGATGGGCCAGCTCCATCTCAGTCAACTACTTTGAGTCACTAC AGAAGGAATCTATCA |
| 23 | budCtobdhF1-GGATCCCCGCATCACCGGCAAAGCGGGC |
| 24 | budCtobdhR1-CTCCATGCCATCTCAATGCTTGCATTGATAGAT TCCTTCGTAGTGAC |
| 25 | budCtobdhF2-TCACTACAGAAGGAATCTATCAATGCAAGCATT GAGATGGCATGGAG |
| 26 | budCtobdhR2-CAAACCATGTCAGAGCTTATTTATTATTAGGCT TTCGGAGATACCAGGAT |
| 27 | TAATAAATAAGCTCTGACATGGTTTGCCCCGGCGTCACCGCCGGGG CTTTTTTATTTCAACCTTTAGGGAAGATCCACAGGTCGCTGACGGG CAATGTCAGATGGCAACGCTCGGCATCGCGCAGCGCGCTGACGGG GCGCGTATGGCGAAATCATCGCCTTCAGTGCGAAACAGATACTCCC AGCCGTCGCCGAGGTACATGCTGGTCAACAGCGGCAGCGCCAGCAT GTTCTCTTCAGGCGCGGAAAGCGATGCGCAAACGCTCAACGCGGATC ACCGCCGTCGCCTCTTCCCCCACGCTAACCCCTTCCCCCGCCATTC CCCATAGCGCCCAGCTGGCCCCCTCAATGCGCGCCCGACCGTTCTC CAGCGCGCTAACGGTGCCATGCAGGCGATTATTACTGCCCATAAAC TCGGCGGCAAACAGCGTTTTCGGGCTGCCGTACATCCTGCGGGG TTCCCTGCTGCTCGATCACGCCGTTGTTAAGCAGCAGAATGCGATC GGAAATCGCCATCGCCTCATTCTGATCGTGGGTGACCATCAGCGCC GAAAGCCCCAGCTTGACGATCAGCTCGCGCAAAAAGACCCGCGCTT CTTCCCGCAGCTTGGCGTCCAGATTCGACAGCGGTTCATCCAGCAG GATCACCGGCGGGTTGTAAACCAGCGCCCTGCCGATGGCCACGCGC TGCTGCTGTCCTCCGGAGAGCTGATGCCCATGGCGACTGCCAAGAT GCCCCAGCCCAAGCTGTTCAAGTACGGTCTGGACCCGTTGCTTGAT CTCCGCGGCGGCAACCTTACGCAGCTTCAGCGGGTAAGCGACGTTT TCAAACACCGTTTTATGCGGCCACAGCGCATAGGACTGAAACACCA GACCCAGGTTACGCTCCTCGGCCGGAATTTCGCTACGCGGGTTGCC GTCATAGACGCGGGATTTTCCAATGGTAATAATGCCGCCGGTCGGC TTCTCCAGCCCGGCGACCGCCCGCAGCAGCGTGGTTTTTCCGCTGC CCGATGGCCCGAGCAGCGACACCACCTCTCCCCGCTTCAGTTCCAT GGACACGCCCTTCAGTACCGGATTATCGCCATAGGTCAGATGCAGG TTTTCTACCGATAATTCAATCATGTAATTTCACTCCAAAGCGCAGG GCGATACCCAGACCGACGACCACCAGCAGGATATTAATAAAGGAGA GCGCGGCGACGATATCGATAGCCCCGCCGCCCACAGCGAGACCAG CATCGAACCAATCGTTTCGGTTCGGGCGAAGCAGATAGACCCCG GTGGAGTATTCGCGCTCGAAGATAAGAAACATCAGCAGCCAGGAGC CGATTAAGCCGTAGCGCGACAGCGGCACCGTAACGTGACGGGTAAT CTGCCCGCGCGATGCGCCGGTACTGCGCGCGGCCTCTTCCAACTCC GGCGCTACCTGCAGCAGCGTCGAGGAGATCAGCCGCAGGCCGTAAG CCATCCACACCACGGTATAGGCCAGCCA |

TABLE 5-continued

| SEQ ID NO | Sequence |
|---|---|
| 28 | budCtobdhF3-ATCCTGGTATCTCCGAAAGCCTAATAATAAATAAGCTCTGACATGGTTTG |
| 29 | budCtobdhR3-GCGGCCGCTGGCTGGCCTATACCGTGGTGTG |
| 30 | CCGCATCACCGGCAAAGCGGGCGTCGCGCTGGTCACGTCCGACCGGGCTGCTCTAACCTGATTACCGGGATGGCAACGGCCAATAGCGAAGGCGACCCGGTGGTGGCGCTGGGCGGCGCGGTAAAACGCGCCGACAAGGCCAAACAGGTGCACCAGAGTATGGATACGGTGACGATGTTTAGCCCGGTGACCAAATACTCGGTGGAAGTCACCGCGCCGGAAGCGCTGGCGGAAGTTGTCTCCAACGCGTTTCGTGCAGCCGAGCAGGGACGCCCCGGCAGCGCCTTCGTCAGCCTGCCGCAGGACGTGGTCGACGGGCCGGTCCACGCCAGGGTTCTGCCCGCCGGCGATGCGCCGCAGACCGGCGCGGCGCCGGACGACGCCATTGCGCGAGTCGCGAAGATGATTGCCGGCGCGAAAAATCCGATATTTCTGCTCGGCCTGATGGCCAGCCAGACGGAAAACAGCGCGGCGCTGCGCGAATTGCTGAAAAAAAGTCATATCCCGGTGACCAGCACCTATCAGGCCGCCGGCGCAGTCAATCAGGATCACTTTACCCGCTTCGCCGGACGGGTTGGTCTGTTCAACAACCAGGCAGGGGATCGACTCCTGCATCTCGCCGACCTGGTCATCTGCATCGGCTATAGTCCGGTGGATACGAGCCGGCCATGTGGAATAACGGTAACGCCACGCTGGTACATATCGACGTGCTGCCCGCTTACGAAGAGCGTAATTATACCCCGGACGTCGAGCTGGTCGGCAATATCGCCGCCACCCTGAACAAACTGTCTCAACGCATCGACCACCAGCTGGTGCTCTCGCCGCAGGCCGCCGAGATCCTTGTCGACCGCCAGCATCAGCGGGAGCTCCTCGACCGCCGCGGTGCGCACCTGAACCAGTTCGCGCTTCATCCGCTGCGCATCGTTCGCGCCATGCAGGACATCGTCAATAGCGATGTCACCCTGACCGTCGATATGGGGAGCTTTCATATCTGGATCGCCCGCTATCTCTACAGCTTTCGCGCCCGTCAGGTCATGATTTCCAACGGTCAACAGACCATGGGCGTGGCGCTGCCGTGGGCGATTGGCGCCTGGCTGGTCAATCGCAGCGCAAAGTGGTTTCCGTTTCCGGCGACGGCGTTTCCTGCAGTCCAGCATGGAGCTGGAGACCGCTGTACGGCTGAAAAGCGAACGTCCTGCATATCATCTGGGTCGATAACGGCTACAACATGGTGGCGATTCAGGAGGAGAAAAAATACCAGCGGCTCTCCGGCGTTGAGTTCGGCCCGGTGGATTTTAAAGTCTACGCCGAAGCCTTCGGCGCCAAAGGGTTTGCGGTAGAGAGCGCCGAAGCCCTTGAGCCGACGCTGCGGGCGGCGATGGACGTGACGGCCCCGCCGTCGTAGCCATCCCCGTGGATTACCGCGATAACCCGCTGCTGATGGGCCAGCTCCATCTCAGTCAACTACTTTGAGTCACTACAGAAGGAATCTATCAATGCAAGCATTGAGATGGCATGGAGTAAAAGATTTACGTTTGGAAAACATTGAGCAACCCGCTGCTCTTCCAGGAAAAGTAAAAATCAAGTAGAATGGTGTGGCATTTGCGGAAGTGATCTTCACGAATATGTAGCAGGACCGATCTTCATTCCTGAAAACGCTCAGCATCCACTGACTGGCGAAAAAGCTCCGATTGTGATGGGACATGAATTTTCTGGACAAGTCGTTGAAATCGGTGAAGGTGTAACTAAAATTCAGGTTGGCGACCGTGTAGTCGTAGAACCGGTTTTTGCATGTGGAGAATGTGATGCATGTAGACAAGGCAAATATAACCTTTGCGATAAATGGGCTTCCTCGGTTTGGCAGGCGGCGGCGGTGGATTTTCTGAATATGTCGCAGCTGACGAGCACATGGTTCACAAAATTCCAGAAAGCGTATCCTTCGAGCAAGGCGCTTTGGTAGAGCCTTCGGCCGTTGCTTTGTACGCTGTACGTCAAAGCCAACTGAAAGTCGGCGACAAAGCTGTCGTGTTTGGCGCTGGTCCTATCGGATTGCTGGTTATTGAAGCGTTGAAAGCTTCGGGCGCATCTGAGATTTATGCAGTAGAGCTTTCCGAGGAGCGTAAAGCTAAAGCTGAAGAGCTGGGTGCTATTGTGCTTGATCCTAAAACTTATGATGTTGTGGAAGAACTGCACAAACGGACCAACGGTGGCGTAGATGTAGCCTATGAAGTCACTGGAGTACCTCCTGTGCTGACTCAAGCGATTGAATCCACTAAAATTAGCGGACAAATCATGATCGTCAGCATTTTTGAAAAGAAGCTCCAATCAAACCGAACAATATCGTTATGAAGGAACGCAATCTGACTGGTATTATCGGCTACCGTGATGTATTCCCGGCTGTCATCAGCTTGATGGAAAAGGGTATTTCCCTGCTGACAAGCTTGTGACCAAACGTATTAAGCTCGAAGAAGTAATCGAGCAAGGTTTTGAAGGTCTCCTGAAAGAAAAAAATCAGGTTAAAATCCTGGTATCTCCGAAAGCCTAATAATAAATAAGCTCTGACATGGTTTGCCCCGGCGTCACCGCCGGGGCTTTTTATTTCAACCTTTAGGGAAGATCCACAGGTCGCTGACGGGCAATGTCAGATGGCAACGCTCGGCATCGCGCAGCGCGCTGCCGTAGGCGCGTATGGCGAAATCATCGCCTTCAGTGCGAAACAGATACTCCCAGCGGTCGCCGAGGTACATGCTGGTCAACAGCGGCAGCGCCAGCATGTTCTCTTCAGGCGCGGAAGCGATGCGCAAACGCTCAACGCGGATCACCGCCGTCGCCTCTTCCCCCACGCTAACCCCTTCCCCCGCCATTCCCCATAGCGCCCAGCTGGCCCCTCAATGCGCGCCCGACCGTTCTCCAGCGCGCTAACGGTGCCATGCAGGCGATTATTACTGCCCATAAACTCGGCGGCAAACAGCGTTTTCGGGCTGCCGTACATCTCCTGCGGGGTTCCCTGCTGCTCGATCACGCCGTTGTTAAGCAGCAGAATGCGATCGGAAATCGCCATCGCCTCATTCTGATCGTGGGTGACCATCAGCGCCGAAAGCCCCAGCTTGACGATCAGCTCGCGCAAAAAGACCCGCGCTTCTTCCCGCAGCTTGGCGTCCAGATTCGACAGCGGTTCATCCAGCAGGATCACCGGCGGGTTGTAAACCAGCGCGCTGCCGATGGCCACGCGCTGCTGCTGTCCTCCGGAGAGCTGATGCGGATGGCGACTGCCAAGATGCCCCAGCCCAAGCTGTTCAAGTACGGTCTGGACCCGTTGCTTGATCTCCGCGGCGGCAACCTTACGCAGCTTCAGCGGGTAAGCGACGTTTTCAAACACCGTTTTATGCGGCCACAGCGCATAGGACTGAAACACCAGACCCAGGTTACGCTCCTCGGCCGGAATTTCGCTACGCGGGTTGCCGTCATAGACGCGGGATTTTCCAATGGTAATAATGCCGCCGGTCGGCTTCTCCAGCCCGGCGACCGCCCGCAGCAGCGTGGTTTTTCCGCTGCCCGATGGCCCGAGCAGCGACACCACCTCTCCCCGCTTCAGTTCCATGGACACGCCCTTCAGTACCGGATTATCGCCATAGGTCAGATGCAGGTTTTCTACCGATAATTCAATCATGTAATTTCACTCCAAAGCGCAGGGCGATACCCAGACCGACGACCACCAGCAGGATATTAATAAAGGAGAGCGCGGCGACGATATCGATAGCCCCCGCCGCCCACAGCGAGACCAGCATCGAACCAATCGTTTCGGTTCCGGGCGAAAGCAGATAGACCCCGGTGGAGTATTCGCGCTCGAAGATAAGAAACATCAGCAGCCAGGAGCCGATTAAGCCGTAGCGCGACAGCGGCACCGTAACGTGACGGGTAATCTGCCCGCGCGATGCGCCGGTACTGCGCGCGGCCTCTTCCAACTCCGGCGCTACCTGCAGCAGCGTCGAGGAGATCAGCCGCAGGCCGTAAGCCATCCACACCACGGTATAGGCCAGCCA |

Strain of *Klebsiella oxytoca* KCTC 12133BP ΔldhA dar$_{Ko}$::bdh$_{Pp}$ (KoΔLB2)

A strain *Klebsiella oxytoca* KCTC 12133BP ΔldhA dar$_{Ko}$::bdh$_{Pp}$ (KoΔLB2) in which a gene encoding darKo as a *Klebsiella oxytoca* KCTC 12133BP innate acetoin reductase is substituted with bdh$_{Pp}$ as a target gene was constructed as follows. Specifically, the recombinant *Klebsiella oxytoca* was constructed using *Klebsiella oxytoca* KCTC 12133BP ΔldhA (Ko ΔldhA) in accordance with the following method. Gene cluster of this strain is depicted in FIG. 3.

Firstly, in order to in-frame substitute dar$_{Ko}$ (SEQ ID NO: 12) of *Klebsiella oxytoca* KCTC 12133BP innate acetoin reductase with bdh$_{Pp}$ (SEQ ID NO: 21) as a target gene, a homologous region 1 (SEQ ID NO: 31) of dar$_{Ko}$ was amplified by PCR using primers of SEQ ID NOs: 32 and 33. In addition, bdh$_{Pp}$ (SEQ ID NO: 21) was amplified by PCR using primers of SEQ ID NOs: 34 and 35. A homologous region 2 (SEQ ID NO: 36) of dar$_{Ko}$ was amplified by PCR using primers of SEQ ID NOs: 37 and 38. Next, the homologous region 1 (SEQ ID NO: 31), bdh$_{Pp}$ (SEQ ID NO: 21), and the homologous region 2 (SEQ ID NO: 36) were amplified by PCR using those regions as templates for PCR, thereby obtaining a completed DNA fragment (SEQ ID NO: 39) in which the homologous region 1, bdh$_{Pp}$, and the homologous region 2 were ligated (Table 6).

The completed DNA fragment may include antibiotic resistance genes and the like in order to enhance the probability of recombination of target genes. Further, the completed DNA fragment may include sacB encoding levansucrase in order to remove antibiotic resistance genes recombined in the chromosomes.

TABLE 6

| SEQ ID NO | Sequence |
|---|---|
| 31 | GCCGCAGACGACGTCGCACAGCGCCGGATGCAGGCGATTAAGCATCGAGGTCTGCAGAAGGAAGTCGAGCACCTCTGGCGGCAGCGGCGCGAAAATCACCTCATCCAGATAGCGGGAGATTGACCGCGAGCCGGCGCTGTGACCCATCGCCGTGGAGGCGTCCGCAGAGAGCGCGGCCATTTTC |

TABLE 6-continued

| SEQ ID NO | Sequence |
|---|---|
| | ATTCCCGCGATCCACCCTTCCGTGAGCGCGATTAGCCGCGGGATCG
CCTGCGGATCCAGCCCCGATGCGCCGGAGAACCAGGCGCGGGCTTC
GCTGGGGGTAAAGCGCAGCTCGGGGTCGTACACCTCCAGCAGCTGA
TCCTGCATATGCAGACGGCTGAGGGCTAAAGACGGCTGACTGCGGC
TACCGATAATCAGGTGCAGCGCCGGCGGCGCATGGTCCAGCAGCCA
GCTCATTCCCTGATGAATCGCCGGATCGCTGATGCATTGATAGTCG
TCGAGGATCAGATACAGCGGGTGCGGGCACTGATTAAGCTGATTAA
CGAGTTCAGCAAAGAACAGGGGGAGGTCGGCCGGAAGCTCGCCTTG
CAGCAGCTGCAGAAACGACGGGCTCCACCCCTGCCACAAGGGCCGC
AGCGCCTCCTGCAGATAGCGTATAAACAGTAGCGGCGCGTTGTCAT
CCTCTTCAAGGCTCAGCCAGGCCAGCGCATCCCCTTGTCGAAGGCG
GTGTCGATACCACTGCGCCAGCAGGGTGGTTTTGCCAAATCCGGCG
GGCGCGCGCACCAGGGTTAAACGGCGGGAGACGGCGGCGTCGAAGG
GCTGTAGCAGGCGCTCCCGCGATAGCAGACTTTCCGGCGTACGGGG
CGGCGTAAAGCGCGTGGAGATAAGCGGCAGCGTCCCCGTGAAGCGT
AAAGGTTCCTGATGAACAAGCGCTGCCAGCGCATCATCCGCCGAGG
ATAAAAAGGCCATACCACGATTACTCCTTAATCCAGTCCGTACGCT
CATTATCCCCCCATCAGGGGGTAGGCCACGCTTATCGCGCCCGA
TAGAGTAGTGCCATTCGCCGCAGCGGCTACGACGACATCGGCCGCG
GGCCTCCCTAGTTTATTAATCAGTACAAGGTGAGTACAGAC |
| 32 | dartobdhF1-TCGACTCTAGAGCCGCAGACGACGTCGCACAGC |
| 33 | dartobdhR1-CATGCCATCTCAATGCTTGCATGTCTGTACTCAC
CTTGTACTG |
| 34 | dartobdhF2-CAGTACAAGGTGAGTACAGACATGCAAGCATTGA
GATGGCATG |
| 35 | dartobdhR2-CTGCGCCGGGTTTATCCCTTAGGCTTTCGGAGAT
ACCAGG |
| 36 | GGGATAAACCCGGCGCAGAACGCGCCGGGTTTTTGCGGGGTTACG
CGTTAGCCGCGGGCTCCTGCGGCTTGTCGCTACGGGTGTTTTCCA
GCATCCGGCGAACCGGAACAATCAGCAGGCACAGCACCGCGGCGC
AGATCAGCAGCGCAATAGAGCAGCGTGCGAACAGGTCGGGCAGCA
TATCCAGCTGATCGGCCTTCACGTGACCGCCAATCAGACCCGCCG
CCAGGTTCCCCAGGGCGCTGGCGCAGAACCACGACCCATCATCT
GGCCGCGCATTCTTTCCGGCGCCAGCAGCGTCATGGTCGCGAGGC
CAATCGGGCTGAGGCACAGCTCGCCCAGCGTCAGCATCAGAATAC
TGCCCACCAGCCACATCGGCGAGACGCCCGCGCCGTTGTTGCTCA
GGACGTTTTGCGCCGGCGCATCATCAGGCCAAAGCCCGCGACCG
CGCATAAAATACCGATAACAAACTTGGTGATGCTGCTCGGACGCA
CGTTTTTACGCGCCAGCGCAGGCCACGCCCAGCTAAATACCGGCG
CCAGCAGAATAATAAACAGGGCGTTAATCGACTGGAACCACACCG
CCGGGATCTCGAAGGAGCCGAGCATACGGTTGTATAGTCGTTAG
CGAACAGGTTAAACGAGGTCGGTTTCTGCTCAAACGTCGACCAGA
AAAAGGCGGCAGAGATCAGCAGGATAAAGCATACCAGCAGGCGGG
CGCGCTCTTTGCGGCTCAATCCGGCGAAGACGAACAGGTAGATAA
AATAGAGTACCACCGACCGCCGCAATCACGTAGACCAGGCTGTCC
CGACCGCCACCGGGTTAATCACGATAACGCCCTGGGCAATCAAGG
CGATGATAACCGCCACGCCCACCGTTAGCGCCAGCAACCATGCGC
CGACGCCATTTCGTTTCACTACCGGGCTGTTCCAGGTGGAATCGA
GGCCGACTTCACTGTCGTAGCGTTTCATCGCCGGACGGCAAAAA
CGCGGAAGATAATCAGCGCGACCAGCATCCCGATGCCGCCGATGC
CGAAGCCCCAGTGCCAGCCGTGGGATTAATCAGCCAGCCGGAGA
TCAGCGGGGCGATAAACGACCCCATGTTGATGCCCATATAAAACA
GCGAGAAGCCGCCATCGCGCGCGCATCGCCTTTTTTGTAGAGGG
TACCGACCATCCACGAAATACAGGTTTTAAACAGGCCGGAATAA
GCACGATAAACATCAGGCCAATAAAGAACAGGCTATCGCCCATCA
CCGCCGACAGGGCGATGGAGAGATGGCCCAGAGCGATCAGTATCG
AACCGTACCAGACCGCCTTTTGTTGCCCGAGCCAGTTATCAGCCA
GCCAGCCGCCCGCAGCGCGGCAAGATACATGTCCCGGCAAGA
TCCCGACAATGGCCGCGCGTTCTCGCCGCCTCGCCCCATCCCAC
CGTCATAGACGGTGGCCGCCATAAACAGGATCAGTCAACGGACGAA
TACCGTAAAACGAGA |
| 37 | dartobdhF3-CCTGGTATCTCCGAAAGCCTAAGGGATAAACCCG
GCGCAG |
| 38 | dartobdhR3-GATCGCGGCCGCTCTCGTTTTACGGTATTCGTCC
GTTAC |
| 39 | GCCGCAGACGACGTCGCACAGCGCCGGATGCAGGCGATTAAGCAT
CGAGGTCTGCAGAAGGAAGTCGAGCACCTCTGGCGGCAGCGCGCG
GAAAATCACCTCATCCAGATAGCGGGAGATTGACCGCGAGCCGGC |

| SEQ ID NO | Sequence |
|---|---|
| | GCTGTGACCCATCGCCGTGGAGGCGTCCGCAGAGAGCGCGGCCAT
TTTCATTCCCGCGATCCACCCTTCCGTGAGCGCGATTAGCCGCGG
GATCGCCTGCGGATCCAGCCCCGATGCGCCGGAGAACCAGGCGCG
GGCTTCGCTGGGGGTAAAGCGCAGCTCGGGGTCGTACACCTCCAG
CAGCTGATCCTGCATATGCAGACGGCTGAGGGCTAAAGACGGCTG
ACTGCGGCTACCGATAATCAGGTGCAGCGCCGGCGGCGCATGGTC
CAGCAGCCAGCTCATTCCCTGATGAATCGCCGGATCGCTGATGCA
TTGATAGTCGTCGAGGATCAGATACAGCGGGTGCGGGCACTGATT
CCAAGCTGATTAACGAGTTCAGCAAAGAACAGGGGGAGGTCGGCC
GGAAGCTCGCCTTGCAGCAGCTGCAGAAACGACGGGCTCCACCCC
TGCCACAAGGGCCGCAGCGCCTCCTGCAGATAGCGTATAAACAGT
AGCGGCGCGTTGTCATCCTCTTCAAGGCTCAGCCAGGCCAGCGCA
TCCTTGTCGAAGGCGGTGTCGATACCACTGCGCCAGCAGGGTGGT
TTTGCCAAATCCGGCGGGCGCGCACCAGGGTTAAACGGCGGGA
GACGGCGGCGTCGAGGCGCTGTAGCAGGCGCTCCCGCGATAGCAG
ACTTTCCGGCGTACGGGCGGCGTAAAGCGCGTGGAGATAAGCGG
CAGCGTCCCCGTGAAGCGTAAAGGTTCCTGATGAACAAGCGCTGC
CAGCGCATCATCCGCCGAGGATAAAAAGGCCATACCACGATTACT
CCTTAATCCAGTCCGTACGCTCATTATCCCCCCATCAGGGGGT
AGGCCACGCTTATCGCGCCCGATAGAGTAGTGCCATTCGCCGCAG
CGGCTACGACGACATCGGCCGCGGGCCTCCCTAGTTTATTAATCA
GTACAAGGTGAGTACAGACATGCAAGCATTGAGATGGCATGGAGT
AAAAGATTTACGTTTGGAAAACATTGAGCAACCCGCTGCTCTTCC
AGGAAAAGTAAAAATCAAAGTAGAATGGTGTGGCATTTGCGGAAG
TGATCTTCACGAATATGTAGCAGGACCGATCTTCATTCCTGAAAA
CGCTCAGCATCCACTGACTGGCGAAAAAGCTCCGATTGTGATGGG
ACATGAATTTTCTGGACAAGTCGTTGAAATCGGTGAAGGTGTAAC
TAAAATTCAGGTTGGCGACCGTGTAGTCGTAGAACCGGTTTTTGC
ATGTGGAGAATGTGATGCATGTAGACAAGGCAAATATAACCTTG
CGATAAAATGGGCTTCCTCGGTTTGGCAGGCGGCGGCGGTGGATT
TTCTGAATATGTCGCAGCTGACGAGCACATGGTTCACAAAATTCC
AGAAAGCGTATCCTTCGAGCAAGGCGCTTTGGTAGAGCCTTCGGC
CGTTGCTTTGTACGCGTGTACGTCAAAGCCAACTGAAAGTCGGCGA
CAAAGCTCGTGTTTGGCGCTGGTCCTATCGGATTGCTGGTTAT
TGAAGCGTTGAAAGCTTCGGGCGCATCTGAGATTTATGCAGTAGA
GCTTTCCGAGGAGCGTAAAGCTAAAGCTGAAGAGCTGGGTGCTAT
TGTGCTTGATCCTAAAACTTATGATGTTGTGGAAGAACTGCACAA
ACGGACCAACGGTGGCGACGTAGCGTATGAAGTCACTGGAGT
ACCTCCTGTGCTGACTCAAGCGATTGAATCCACTAAAATTAGCGG
ACAAATCATGATCGTCAGCATTTTTGAAAAAGAAGCTCCAATCAA
ACCGAACAATATCGTTATGAAGGAACGCAATCTGACTGGTATTAT
CGGCTACCGTGATGTTATTCCCGCTGTCATCAGCTTGATGGAAAA
AGGGTATTTCCCTGCTGACAAGCTTGTGACCAAACGTATTAAGCT
CGAAGAAGTAATCGAGCAAGGTTTTGAAGGTCTCCTGAAAGAAAA
AAATCAGGTTAAAATCCTGGTATCTCCGAAAGCCTAAGGGATAAA
CCCGGCGCAGAACGCGCCGGGTTTTTGCGGGGTTACGCGTTAGCC
GCGGGCTCCTGCGGCTTGTCGCTACGGGTGTTTTCCAGCATCCGG
CGAACCGGAACAATCAGCAGGCACAGCACCGCGGCGCAGATCAGC
AGCGCAATAGAGCAGCGTGCGAACAGGTCGGGCAGCATATCCAGC
TGATCGGCCTTCACGTGACCGCCAATCAGACCCGCCGCCAGGTTC
CCCAGGGCGCTGGCGCAGAACCACGACCCATCATCTGGCCGCGC
ATTCTTTCCGGCGCCAGCAGCGTCATGGTCGCGAGGCCAATCGGG
CTGAGGCACAGCTCGCCCAGCGTCAGCATCAGAATACTGCCCACC
AGCCACATCGGCGAGACGCCCGCGCCGTTGTTGCTCAGGACGTTT
TGCGCCGGCGCATCATCAGGCCAAAGCCCGCGACCGCGCATAAA
ATACCGATAACAAACTTGGTGATGCTGCTCGGACGCACGTTTTTA
CGCGCCAGCGCAGGCCACGCCCAGCTAAATACCGGCGCCAGCAGA
ATAATAAACAGGGCGTTAATCGACTGGAACCACACCGCCGGGATC
TCGAAGGAGCCGAGCATACGGTTGTATAGTCGTTAGCGAACAGGT
TAAACGAGGTCGGTTTCTGCTCAAACGTCGACCAGAAAAAGGCG
GCAGAGATCAGCAGGATAAAGCATACCAGCAGGCGGGCGCGCTCT
TTGCGGCTCAATCCGGCGAAGACGAACAGGTAGATAAAATAGAGT
ACCACCGACCGCCGCAATCACGTAGACCAGGCTGTCCCGACCGCC
ACCGGGTTAATCACGATAACGCCCTGGGCAATCAAGGCGATGATA
ACCGCCACGCCCACCGTTAGCGCCAGCAACCATGCGCCGACGCCA
TTTCGTTTCACTACCGGGCTGTTCCAGGTGGAATCGAGGCCGACT
TCACTGTCGTAGCGTTTCATCGCCGGACGGCAAAAACGCGGAAG
ATAATCAGCGCGACCAGCATCCCGATGCCGCCGATGCCGAAGCCC
CAGTGCCAGCCGTGGGATTAATCAGCCAGCCGGAGATCAGCGGG
GCGATAAACGACCCCATGTTGATGCCCATATAAAACAGCGAGAAG
CCGCCATCGCGCGCGCATCGCCTTTTTTGTAGAGGGTACCGACCA
TCCACGAAATACAGGTTTTAAACAGGCCGGAATAAGCACGATA
AACATCAGGCCAATAAAGAACAGGCTATCGCCCATCACCGCCGAC
AGGGCGATGGAGAGATGGCCCAGAGCGATCAGTATCGAACCGTAC
CAGACCGCCTTTTGTTGCCCGAGCCAGTTATCAGCCAGCCAGCCG
CCCGGCAGCGCGGCAAGATACATGGTCCCGGCAAAGATCCCGACA |

TABLE 6-continued

| SEQ ID NO | Sequence |
|---|---|
| | ATGGCCGACGCGTTCTCGCGCGCCAGCCCCATCCCACCGTCATAG ACGGTGGCCGCCATAAACAGGATCAGTAACGGACGAATACCGTAA AACGAGA |

Strain of Klebsiella oxytoca KCTC 12133BP ΔldhA Δdar$_{Ko}$ budC$_{Ko}$::Bdh$_{Pp}$ (KoΔLB3)

A strain of Klebsiella oxytoca KCTC 12133BP ΔldhA Δdar$_{Ko}$ budC$_{Ko}$::bdh$_{Pp}$ (KoΔLB3) was constructed using the previously constructed Klebsiella oxytoca KCTC 12133BP ΔldhA Δdar$_{Ko}$ as a base strain. The method for in-frame substituting budC$_{Ko}$ (SEQ ID NO: 10) as one of genes encoding innate acetoin reductases in the base strain with bdh$_{Pp}$ (SEQ ID NO: 21) as a target gene was identical to the method employed in constructing the strain of "Klebsiella oxytoca KCTC 12133BP ΔldhA budC$_{Ko}$::bdh$_{Pp}$ (KoΔLB1)" (FIG. 3).

The genotypes of recombinant strains of Klebsiella oxytoca KCTC 12133BP are summarized in Table 7.

TABLE 7

| Strains | Genotypes | Description |
|---|---|---|
| KoΔL | ΔldhA | ldhA deleted Klebsiella oxytoca KCTC 12133BP (comparison strain) |
| KoΔLB1 | ΔldhA budC$_{Ko}$::bdh$_{Pp}$ | Klebsiella oxytoca KCTC 12133BP in which ldhA is deleted and budC$_{Ko}$ substituted with bdh$_{Pp}$ |
| KoΔLB2 | ΔldhA dar$_{Ko}$::bdh$_{Pp}$ | Klebsiella oxytoca KCTC 12133BP in which ldhA is deleted and dar$_{Ko}$ is substituted with bdh$_{Pp}$ |
| KoΔLB3 | ΔldhA Δdar$_{Ko}$ budC$_{Ko}$::bdh$_{Pp}$ | Klebsiella oxytoca KCTC 12133BP in which ldhA and dar$_{Ko}$ are deleted and budC$_{Ko}$ is substituted with bdh$_{Pp}$ |

<Experimental Example 2> Production of 2,3-Butanediol Through Batch Fermentation The recombinant strains constructed in Experimental Example 1 were cultured, thereby producing 2,3-butanediol. As a control for comparison, Klebsiella oxytoca KCTC 12133BP ΔldhA (KO ΔL) was used.

250 ml of a complex medium containing 9 g/L glucose (50 mM, glucose) was inoculated with each recombinant strain, followed by culturing at 37° C. for 16 hours. The resulting culture solution was injected into 3 L of complex medium, which was then subjected to fermentation. The fermentation conditions were as follows: microaerobic conditions (aeration rate of 1 vvm, stirring speed of 400 rpm), 90 g/L of initial glucose concentration, pH 6.8, a cultivation temperature of 37° C. While fermenting, 5N NaOH was used in order to adjust pH. Samples were taken while fermenting using the recombinant Klebsiella. The growth rate was determined by measuring OD600 (optical density) of the sampled specimens. The sampled specimens were subjected to centrifugation at 13,000 rpm for 10 minutes, followed by assaying the concentration of metabolites and 2,3-butanediol in the supernatant by high performance liquid chromatography (HPLC). In addition, the produced 2,3-butanediol isomers were assayed by gas chromatography (GC).

As a result, the recombinant strains constructed in Experimental Example 1 exhibited similar growth and productivity to the strain KO ΔL as a comparative strain. KoΔLB3 showed the best performance in terms of D(-) 2,3-butanediol production. Namely, the strain in which one acetoin reductase budC$_{Ko}$ of two acetoin reductases in Klebsiella oxytoca KCTC 12133BP was substituted with bdh$_{Pp}$, and dar$_{Ko}$ as the other acetoin reductases in Klebsiella oxytoca KCTC 12133BP was deleted showed similar 2,3-butanediol productivity, production concentration, and production yield to the comparison strain while producing D(-) 2,3-butanediol with purity (namely, ratio) of 97% or more (FIG. 4, Table 8).

TABLE 8

| | 2,3-butanediol isomers | | | | | | Total Yield |
|---|---|---|---|---|---|---|---|
| | D(-) | | L(+) | | meso | | |
| Strains | g/L | %$^a$ | g/L | %$^a$ | g/L | %$^a$ | (g/g) |
| KoΔL | 0.2 | 0.8 | 2.0 | 6.9 | 26.8 | 92.3 | 0.32 |
| KoΔLB1 | 25.1 | 90.0 | 1.2 | 4.4 | 1.6 | 5.6 | 0.32 |
| KoΔLB2 | 6.5 | 22.3 | 3.6 | 12.3 | 19.1 | 65.4 | 0.34 |
| KoΔLB3 | 26.1 | 97.4 | 0 | 0 | 0.7 | 2.6 | 0.31 |

$^a$ratio of 2,3-butanediol isomers

<Experimental Example 3> Production of 2,3-Butanediol Through Fed-Batch Fermentation The strain of KoΔLB3 (Klebsiella oxytoca KCTC 12133BP ΔldhA Δdar$_{Ko}$ budC$_{Ko}$::bdh$_{Pp}$) which was found to be the best in terms of D(-) 2,3-butanediol productivity among the strains identified to have D(-) 2,3-butanediol productivity in Experimental Example 2 was further examined for its productivity through fed-batch fermentation.

250 ml of a complex medium containing 9 g/L glucose (50 mM, glucose) was inoculated with the recombinant strain KoΔLB3, followed by culturing at 37° C. for 16 hours. The resulting culture solution was injected into 3 L of complex medium, which was then subjected to fermentation. The fermentation conditions were as follows: microaerobic conditions (aerobic speed of 1 vvm, stirring rate of 400 rpm), 90 g/L of initial glucose concentration, pH 6.8, and cultivation temperature of 37° C. While fermenting, 5N NaOH was used in order to adjust pH. When glucose concentration during fermentation declined to 10 g/L or less, a glucose solution of 700 g/L or more was fed so that an additional carbon source was supplied. Samples were taken while fermenting using the recombinant Klebsiella. The growth rate was determined by measuring OD600 (optical density) of the sampled specimens. The sampled specimens were subjected to centrifugation at 13,000 rpm for 10 minutes, followed by assaying the concentration of metabolites and 2,3-butanediol in the supernatant by high performance liquid chromatography (HPLC). In addition, the produced 2,3-butanediol isomers were assayed by gas chromatography (GC).

As a result, it was confirmed that the purity of D(-) 2,3-butanediol isomers was maintained at 96.4% or more during the entire fermentation process, the production yield was 44%, the productivity was 2.0 g/L/hr, and the final concentration of D(-) 2,3-butanediol was 98 g/L (FIG. 5 and FIG. 6).

INDUSTRIAL APPLICABILITY

The present invention relates to a recombinant microorganism for producing D(-) 2,3-butanediol, wherein a gene encoding an enzyme for converting acetoin into D(-) 2,3- butanediol is introduced into a microorganism having a pathway for converting acetoin into 2,3-butanediol. In addition, the present invention provides a method for producing D(-) 2,3-butanediol using the recombinant microorganism.

BRIEF DESCRIPTION OF THE SEQUENCES PROVIDED IN THE SEQUENCE

SEQ ID NO: 1 is a nucleotide sequence of ldhA gene. SEQ ID NO: 2 is a homologous region 1 of ldhA gene, and SEQ ID NOs: 3 and 4 are primers for amplification of it. SEQ ID NO: 5 is a homologous region 2 of ldhA gene, and SEQ ID NOs: 6 and 7 are primers for PCR amplification of it. SEQ ID NO: 8 is a DNA fragment in which the homologous regions 1 and 2 of ldhA gene are ligated.

SEQ ID NO: 9 is an amino acid sequence of AR1, and SEQ ID NO: 10 is a nucleotide sequence of $budC_{Ko}$ gene that encodes AR1.

SEQ ID NO: 11 is an amino acid sequence of AR2, and SEQ ID NO: 12 is a nucleotide sequence of $dar_{Ko}$ gene that encodes AR2.

SEQ ID NO: 13 is a homologous region 1 of $dar_{Ko}$ as a target gene, and SEQ ID NOs: 14 and 15 are primers for PCR amplification of it.

SEQ ID NO: 16 is a homologous region 2 of $dar_{Ko}$ as a target gene, and SEQ ID NOs: 17 and 18 are primers for PCR amplification of it.

SEQ ID NO: 19 is a DNA fragment in which a homologous region 1 (SEQ ID NO: 13) and a homologous region 2 (SEQ ID NO: 16) of $dar_{Ko}$ are ligated.

SEQ ID NO: 20 is an amino acid sequence of $Bdh_{Pp}$ originated from *Paenibacillus polymyxa* KCTC 1663, and SEQ ID NO: 21 is a nucleotide sequence of $bdh_{Pp}$ gene that encodes $Bdh_{Pp}$.

SEQ ID NO: 22 is a homologous region 1 of $budC_{Ko}$, and SEQ ID NOs: 23 and 24 are primers for PCR amplification of it.

SEQ ID NOs: 25 and 26 are primers for PCR amplification of $bdh_{Pp}$ (SEQ ID NO: 21).

SEQ ID NO: 27 is a homologous region 2 of $budC_{Ko}$, and SEQ ID NOs: 28 and 29 are primers for PCR amplification of it.

SEQ ID NO: 30 is a DNA fragment in which a homologous region 1 (SEQ ID NO: 22) of $budC_{Ko}$, $bdh_{Pp}$ (SEQ ID NO: 21), and a homologous region 2 (SEQ ID NO: 27) of $budC_{Ko}$ are ligated.

SEQ ID NO: 31 is a homologous region 1 of $dar_{Ko}$, and SEQ ID NOs: 32 and 33 are primers for PCR amplification of it.

SEQ ID NOs: 34 and 35 are primers for PCR amplification of $bdh_{Pp}$ (SEQ ID NO: 21).

SEQ ID NO: 36 is a homologous region 2 of $dar_{Ko}$, and SEQ ID NOs: 37 and 38 are primers for PCR amplification of it.

SEQ ID NO: 39 is a DNA fragment in which a homologous region 1 (SEQ ID NO: 31) of $dar_{Ko}$, $bdh_{Pp}$ (SEQ ID NO: 21) and a homologous region 2 (SEQ ID NO: 36) of $dar_{Ko}$ are ligated.

D(-) 2,3-butanediol by using the recombinant microorganism.

The invention claimed is:

1. A recombinant *Klebsiella oxytoca* microorganism for producing D(-) 2,3-butanediol,
   - wherein the recombinant microorganism is transformed with an acetoin reductase gene encoding an enzyme that converts acetoin into D(-) 2,3-butanediol,
   - wherein a gene encoding an enzyme that converts pyruvate into lactate is deleted in the recombinant microorganism,
   - wherein a gene encoding *Klebsiella oxytoca* acetoin reductase 1 (budC$_{Ko}$) and a gene encoding *Klebsiella oxytoca* acetoin reductase 2 (dar$_{Ko}$) are deleted in the recombinant microorganism,
   - wherein the *Klebsiella oxytoca* acetoin reductase 1 and the *Klebsiella oxytoca* acetoin reductase 2 convert acetoin into meso-2,3-butanediol, and
   - wherein the recombinant microorganism has higher D(-) 2,3 butanediol productivity in comparison to a corresponding wild type *Klebsiella oxytoca* microorganism.

2. The recombinant microorganism for producing D(-) 2,3-butanediol according to claim 1, wherein the acetoin reductase gene encoding an enzyme that converts acetoin into D(-) 2,3-butanediol is a *Paenibacillus polymyxa* acetoin reductase (bdh$_{Pp}$) gene.

3. The recombinant microorganism for producing D(-) 2,3-butanediol according to claim 1, wherein the acetoin reductase gene encoding an enzyme that converts acetoin into D(-) 2,3-butanediol comprises the nucleotide sequence set forth in SEQ ID NO: 21.

4. The recombinant microorganism for producing D(-) 2,3-butanediol according to claim 1, wherein the acetoin reductase gene encoding an enzyme that converts acetoin into D(-) 2,3-butanediol is a gene encoding the amino acid sequence set forth in SEQ ID NO: 20.

5. The recombinant microorganism for producing D(-) 2,3-butanediol according to claim 1, wherein the gene encoding *Klebsiella oxytoca* acetoin reductase 1 (budC$_{Ko}$) is a gene encoding a protein having the amino acid sequence set forth in SEQ ID NO: 9, or a gene having the nucleotide sequence set forth in SEQ ID NO: 10.

6. The recombinant microorganism for producing D(-) 2,3-butanediol according to claim 1, wherein the gene encoding *Klebsiella oxytoca* acetoin reductase 2 (dar$_{Ko}$) is a gene encoding a protein having the amino acid sequence set forth in SEQ ID NO: 11 or a gene having the nucleotide sequence set forth in SEQ ID NO: 12.

7. A method for producing D(-) 2,3-butanediol, comprising:
   - inoculating a culture medium with the recombinant microorganism according to claim 1; and
   - culturing the recombinant microorganism to produce D(-) 2,3-butanediol.

8. A recombinant *Klebsiella oxytoca* microorganism for producing D(-) 2,3-butanediol,
   - wherein a gene encoding *Klebsiella oxytoca* acetoin reductase 1 (budC$_{Ko}$) is substituted with an acetoin reductase gene encoding an enzyme that converts acetoin into D(-) 2,3-butanediol in the recombinant microorganism by inserting the acetoin reductase gene encoding an enzyme that converts acetoin into D(-) 2,3-butanediol into the gene encoding *Klebsiella oxytoca* acetoin reductase 1 (budC$_{Ko}$),
   - wherein a gene encoding an enzyme that converts pyruvate into lactate and a gene encoding *Klebsiella oxytoca* acetoin reductase 2 (dar$_{Ko}$) are deleted in the recombinant microorganism,
   - wherein the *Klebsiella oxytoca* acetoin reductase 1 and the *Klebsiella oxytoca* acetoin reductase 2 convert acetoin into meso-2,3-butanediol, and
   - wherein the recombinant microorganism has higher D(-) 2,3 butanediol productivity in comparison to a corresponding wild type *Klebsiella oxytoca* microorganism.

9. The recombinant microorganism for producing D(-) 2,3-butanediol according to claim 8, wherein the acetoin reductase gene encoding an enzyme that converts acetoin into D(-) 2,3-butanediol is a *Paenibacillus polymyxa* acetoin reductase (bdh$_{Pp}$) gene.

10. The recombinant microorganism for producing D(-) 2,3-butanediol according to claim 8, wherein the acetoin reductase gene encoding an enzyme that converts acetoin into D(-) 2,3-butanediol comprises the nucleotide sequence set forth in SEQ ID NO: 21.

11. The recombinant microorganism for producing D(-) 2,3-butanediol according to claim 8, wherein the acetoin reductase gene encoding an enzyme that converts acetoin into D(-) 2,3-butanediol is a gene encoding the amino acid sequence set forth in SEQ ID NO: 20.

12. The recombinant microorganism for producing D(−) 2,3-butanediol according to claim 8, wherein the gene encoding *Klebsiella oxytoca* acetoin reductase 1 ($budC_{Ko}$) is a gene encoding the amino acid sequence set forth in SEQ ID NO: 9, or a gene having the nucleotide sequence set forth in SEQ ID NO: 10.

13. The recombinant microorganism for producing D(−) 2,3-butanediol according to claim 8, wherein the gene encoding *Klebsiella oxytoca* acetoin reductase 2 ($dar_{Ko}$) is a gene encoding the amino acid sequence set forth in SEQ ID NO: 11 or a gene having the nucleotide sequence set forth in SEQ ID NO: 12.

* * * * *

SEQUENCE LISTING

```
<160> NUMBER OF SEQ ID NOS: 39

<210> SEQ ID NO 1
<211> LENGTH: 990
<212> TYPE: DNA
<213> ORGANISM: Klebsiella oxytoca

<400> SEQUENCE: 1
atgaaaatcg ctgtgtatag tacaaaacag tacgacaaga agtatctgca gcatgttaat      60
gatgcatatg gctttgaact ggagtttttt gacttcctgc taaccgaaaa aaccgccaaa     120
accgccaacg gctgtgaagc ggtgtgtatc ttcgtaaacg atgacggtag ccgcccggta     180
cttgaagaac tgaaagccca cggcgtgcag tacatcgcgc tgcgctgcgc ggggttcaac     240
aacgttgacc tcgatgccgc caaagagctg ggcctgcggg tggtgcgcgt cccggcctac     300
tcgccggaag cggtcgctga gcacgcgatc ggcatgatga tgtcgctgaa ccgccgcatt     360
caccgtgcct atcagcgcac ccgcgacgcg aacttctctc tggaagggct gaccggtttc     420
accatgcacg gtaaaaccgc cggcgttatt ggcaccggta aaatcggcgt cgccgcgctg     480
cgcattctta aaggcttcgg tatgcgtctg ctggcgtttg atcccacc aagcgccgcc     540 gcgctggata tgggcgtgga gtatgtcgat cttgaaaccc tgtaccggga gtccgatgtt     600
atctcactgc actgcccact gaccgatgaa aactaccatt tgctgaacca tgccgcgttc     660
gatcgcatga agacgggggt gatgatcatc aacaccagcc gcggcgcgct catcgattcg     720
caggcagcga tcgacgccct gaagcatcag aaaattggcg cgctggggat ggacgtgtat     780
gagaacgaac gcgatctgtt ctttgaagat aagtctaatg acgtgattca ggatgatgtg     840
ttccgccgtc tctccgcctg ccataacgtc ctgtttaccg gtcaccaggc gtttctgacc     900
```

```
gcggaagcgt tgatcagcat ttcgcaaacc accctcgaca acctgcgtca agtggatgca    960
ggcgaaacct gtcctaacgc actggtctga                                     990
```

<210> SEQ ID NO 2
<211> LENGTH: 595
<212> TYPE: DNA
<213> ORGANISM: Artificial
<220> FEATURE:
<223> OTHER INFORMATION: a homologous region 1 of ldhA gene

<400> SEQUENCE: 2

```
atgacgttcg ctaaatcctg cgccgtcatc tcgctgctga tcccgggcac ctccgggcta    60
ctgctgttcg gcaccctggc atcggccagc ccgggacatt tcctgttaat gtggatgagc   120
gccagcctcg gcgctatcgg cggattctgg ctctcgtggc tgacgggcta ccgctaccgg   180
taccatctgc atcgtatccg ctggcttaat gccgaacgcc tcgctcgcgg ccagttgttc   240
ctgcgccgcc acggcgcgtg ggcagtcttt tttagccgct ttctctctcc gcttcgcgcc   300
accgtgccgc tggtaaccgg cgccagcggc acctctctct ggcagtttca gctcgccaac   360
gtcagctccg gctgctctgt gccgctgatc ctgctggcgc aggcgcgtt aagcctcagc    420 ttttgatgaa aggtattgtc ttttaaagag atttcttaac accgcgatat gctctagaat   480
tattactata acctgctgat taaactagtt tttaacattt gtaagattat tttaattatg   540
ctaccgtgac ggtattatca ctggagaaaa gtctttttc cttgcccttt tgtgc         595
```

<210> SEQ ID NO 3
<211> LENGTH: 30
<212> TYPE: DNA
<213> ORGANISM: Artificial
<220> FEATURE:
<223> OTHER INFORMATION: a primer for amplification of the sequence of
      SEQ. ID. NO: 2

<400> SEQUENCE: 3

```
cacggatcca tgacgttcgc taaatcctgc                                      30
```

<210> SEQ ID NO 4
<211> LENGTH: 40
<212> TYPE: DNA
<213> ORGANISM: Artificial
<220> FEATURE:
<223> OTHER INFORMATION: a primer for amplification of the sequence of
      SEQ ID NO: 2

<400> SEQUENCE: 4

```
gcacaaaagg gcaaggaaaa aagacttttc tccagtgata                           40
```

<210> SEQ ID NO 5
<211> LENGTH: 591
<212> TYPE: DNA
<213> ORGANISM: Artificial
<220> FEATURE:
<223> OTHER INFORMATION: a homologous region 2 of ldhA gene

<400> SEQUENCE: 5

```
tatcactgga gaaaagtctt ttttccttgc ccttttgtgc tcccccttcg cgggggggcac    60 attcagataa tccccacaga aattgcctgc gataaagtta caatcccttc atttattaat   120
acgataaata tttatggaga ttaaatgaac aagtatgctg cgctgctggc ggtgggaatg   180
ttgctatcgg gctgcgttta taacagcaag gtgtcgacca gagcggaaca gcttcagcac   240
caccgttttg tgctgaccag cgttaacggg cagccgctga atgccgcgga taagccgcag   300
```

```
gagctgagct tcggcgaaaa gatgcccatt acgggcaaga tgtctgtttc aggtaatatg    360
tgcaaccgct tcagcggcac gggcaaagtc tctgacggcg agctgaaggt tgaagagctg    420
gcaatgaccc gcatgctctg cacggactcg cagcttaacg ccctggacgc cacgctgagc    480
aaaatgctgc gcgaaggcgc gcaggtcgac ctgacgaaaa cgcagctaac gctggcgacc    540
gccgaccaga cgctggtgta taagctcgcc gacctgatga attaataatt a             591
```

<210> SEQ ID NO 6
<211> LENGTH: 40
<212> TYPE: DNA
<213> ORGANISM: Artificial
<220> FEATURE:
<223> OTHER INFORMATION: a primer for PCR amplification of the sequence
      of SEQ ID NO: 5

<400> SEQUENCE: 6

```
tatcactgga gaaaagtctt ttttccttgc cctttttgtgc                          40
```

<210> SEQ ID NO 7
<211> LENGTH: 32
<212> TYPE: DNA
<213> ORGANISM: Artificial
<220> FEATURE:
<223> OTHER INFORMATION: a primer for PCR amplification of the sequence
      of SEQ ID NO: 5

<400> SEQUENCE: 7

```
cctgcggccg ctaattatta attcatcagg tc                                   32
```

<210> SEQ ID NO 8
<211> LENGTH: 1146
<212> TYPE: DNA
<213> ORGANISM: Artificial
<220> FEATURE:
<223> OTHER INFORMATION: a DNA fragment in which the homologous regions
      1 and 2 of ldhA gene are ligated

<400> SEQUENCE: 8

```
atgacgttcg ctaaatcctg cgccgtcatc tcgctgctga tcccgggcac ctccgggcta    60
ctgctgttcg gcaccctggc atcggccagc ccgggacatt tcctgttaat gtggatgagc   120
gccagcctcg gcgctatcgg cggattctgg ctctcgtggc tgacgggcta ccgctaccgg   180
taccatctgc atcgtatccg ctggcttaat gccgaacgcc tcgctcgcgg ccagttgttc   240
ctgcgccgcc acggcgcgtg ggcagtcttt tttagccgct ttctctctcc gcttcgcgcc   300
accgtgccgc tggtaaccgg cgccagcggc acctctctct ggcagtttca gctcgccaac   360
gtcagctccg gctgctctg gccgctgatc ctgctggcgc caggcgcgtt aagcctcagc   420
ttttgatgaa aggtattgtc ttttaaagag atttcttaac accgcgatat gctctagaat   480
tattactata acctgctgat taaactagtt tttaacattt gtaagattat tttaattatg   540
ctaccgtgac ggtattatca ctggagaaaa gtctttttc cttgcccttt tgtgctcccc   600
cttcgcgggg ggcacattca gataatcccc acagaaattg cctgcgataa agttacaatc   660
ccttcattta ttaatacgat aaatatttat ggagattaaa tgaacaagta tgctgcgctg   720
ctggcggtgg gaatgttgct atcgggctgc gtttataaca gcaaggtgtc gaccagagcg   780
gaacagcttc agcaccaccg ttttgtgctg accagcgtta acgggcagcc gctgaatgcc   840
gcggataagc gcaggagct gagcttcggc gaaaagatgc ccattacggg caagatgtct   900
gtttcaggta atatgtgcaa ccgcttcagc ggcacgggca aagtctctga cggcgagctg   960
```

```
aaggttgaag agctggcaat gacccgcatg ctctgcacgg actcgcagct taacgccctg    1020
gacgccacgc tgagcaaaat gctgcgcgaa ggcgcgcagg tcgacctgac ggaaacgcag    1080
ctaacgctgg cgaccgccga ccagacgctg gtgtataagc tcgccgacct gatgaattaa    1140
taatta                                                              1146
```

<210> SEQ ID NO 9
<211> LENGTH: 256
<212> TYPE: PRT
<213> ORGANISM: Klebsiella oxytoca

<400> SEQUENCE: 9

```
Met Lys Lys Val Ala Leu Val Thr Gly Ala Gly Gln Gly Ile Gly Lys
1               5                   10                  15

Ala Ile Ala Leu Arg Leu Val Lys Asp Gly Phe Ala Val Ala Ile Ala
            20                  25                  30

Asp Tyr Asn Asp Ala Thr Ala Gln Ala Val Ala Asp Glu Ile Asn Arg
        35                  40                  45

Ser Gly Gly Arg Ala Leu Ala Val Lys Val Asp Val Ser Gln Arg Asp
    50                  55                  60

Gln Val Phe Ala Ala Val Glu Gln Ala Arg Lys Gly Leu Gly Gly Phe
65                  70                  75                  80

Asp Val Ile Val Asn Asn Ala Gly Val Ala Pro Ser Thr Pro Ile Glu
                85                  90                  95

Glu Ile Arg Glu Glu Val Ile Asp Lys Val Tyr Asn Ile Asn Val Lys
            100                 105                 110

Gly Val Ile Trp Gly Ile Gln Ala Ala Val Glu Ala Phe Lys Lys Glu
        115                 120                 125

Gly His Gly Gly Lys Ile Ile Asn Ala Cys Ser Gln Ala Gly His Val
    130                 135                 140

Gly Asn Pro Glu Leu Ala Val Tyr Ser Ser Ser Lys Phe Ala Val Arg
145                 150                 155                 160

Gly Leu Thr Gln Thr Ala Ala Arg Asp Leu Ala His Leu Gly Ile Thr
                165                 170                 175

Val Asn Gly Tyr Cys Pro Gly Ile Val Lys Thr Pro Met Trp Ala Glu
            180                 185                 190

Ile Asp Arg Gln Val Ser Glu Ala Ala Gly Lys Pro Leu Gly Tyr Gly
        195                 200                 205

Thr Gln Glu Phe Ala Lys Arg Ile Thr Leu Gly Arg Leu Ser Glu Pro
    210                 215                 220

Glu Asp Val Ala Ala Cys Val Ser Tyr Leu Ala Gly Pro Asp Ser Asn
225                 230                 235                 240

Tyr Met Thr Gly Gln Ser Leu Leu Ile Asp Gly Gly Met Val Phe Asn
                245                 250                 255
```

<210> SEQ ID NO 10
<211> LENGTH: 768
<212> TYPE: DNA
<213> ORGANISM: Klebsiella oxytoca

<400> SEQUENCE: 10

```
atgaaaaaag tcgcactcgt caccggcgcg ggccagggta tcggtaaagc tatcgccctt    60
cgtctggtga agatgggttt tgccgtggct atcgccgatt ataacgacgc caccgcgcag   120
```

```
gcggtcgctg atgaaattaa ccgcagcggc ggccgggcgc tagcggtgaa ggtggatgtg    180
tctcaacgcg atcaggtttt tgccgccgtc aacaggcgc gcaagggtct cggcggtttt     240
gacgtgatcg tcaacaacgc cggggttgcg ccctccacac caatcgaaga gattcgcgag    300
gaggtgatcg ataaagtcta caatatcaac gttaaaggcg ttatctgggg catccaggcc    360
gcggtagagg cgtttaaaaa agagggccac ggcggcaaaa ttatcaacgc ctgctcccag    420
gcgggccatg taggtaaccc ggagctggcg gtctatagct ccagtaaatt tgccgtgcgc    480
ggcctgacgc aaaccgccgc ccgcgatctg gcgcatctgg ggattaccgt aaacggctac    540
tgcccgggga tcgtcaaaac cccaatgtgg gcggaaattg accgccaggt ttccgaagcg    600
gcgggtaaac cgctgggcta cggaacccag gagttcgcca acgcattac ccttgggcgg     660 ctatccgagc cggaagacgt cgcagcctgc gtctcttatc tcgccggtcc ggactccaat    720
tatatgaccg ccaatcgct gctgatcgat ggcggcatgg tatttaac                  768
```

```
<210> SEQ ID NO 11
<211> LENGTH: 259
<212> TYPE: PRT
<213> ORGANISM: Klebsiella oxytoca

<400> SEQUENCE: 11

Met Ala Ile Glu Asn Lys Val Ala Leu Val Thr Gly Ala Gly Gln Gly
1               5                   10                  15

Ile Gly Arg Gly Ile Ala Leu Arg Leu Ala Lys Asp Gly Ala Ser Val
                20                  25                  30

Met Leu Val Asp Val Asn Pro Glu Gly Ile Ala Ala Val Ala Ala Glu
            35                  40                  45

Val Glu Ala Leu Gly Arg Lys Ala Ala Thr Phe Val Ala Asn Ile Ala
        50                  55                  60

Asp Arg Ala Gln Val Tyr Ala Ala Ile Asp Glu Ala Glu Lys Gln Leu
65                  70                  75                  80

Gly Gly Phe Asp Ile Ile Val Asn Asn Ala Gly Ile Ala Gln Val Gln
                85                  90                  95

Ala Leu Ala Asp Val Thr Pro Glu Glu Val Asp Arg Ile Met Arg Ile
            100                 105                 110

Asn Val Gln Gly Thr Leu Trp Gly Ile Gln Ala Ala Lys Lys Phe
        115                 120                 125

Ile Asp Arg Gln Gln Lys Gly Lys Ile Ile Asn Ala Cys Ser Ile Ala
130                 135                 140

Gly His Asp Gly Phe Ala Leu Leu Gly Val Tyr Ser Ala Thr Lys Phe
145                 150                 155                 160

Ala Val Arg Ala Leu Thr Gln Ala Ala Ala Lys Glu Tyr Ala Ser Arg
                165                 170                 175

Gly Ile Thr Val Asn Ala Tyr Cys Pro Gly Ile Val Gly Thr Gly Met
            180                 185                 190

Trp Thr Glu Ile Asp Lys Arg Phe Ala Glu Ile Thr Gly Ala Pro Val
        195                 200                 205

Gly Glu Thr Tyr Lys Lys Tyr Val Glu Gly Ile Ala Leu Gly Arg Ala
    210                 215                 220

Glu Thr Pro Asp Asp Val Ala Ser Leu Val Ser Tyr Leu Ala Gly Pro
225                 230                 235                 240

Asp Ser Asp Tyr Val Thr Gly Gln Ser Ile Leu Ile Asp Gly Gly Ile
                245                 250                 255

Val Tyr Arg
```

<210> SEQ ID NO 12
<211> LENGTH: 777
<212> TYPE: DNA
<213> ORGANISM: Klebsiella oxytoca

<400> SEQUENCE: 12

| | | | | | | |
|---|---|---|---|---|---|---|
| atggctatcg | aaaataaagt | tgcgctggta | accggcgccg | gtcagggcat | tggccgcggt | 60 |
| attgcgttgc | gtctggccaa | agacggcgcg | tcggtgatgc | tggtcgacgt | gaaccctgaa | 120 |
| gggattgccg | ccgtcgccgc | cgaagtggaa | gcgctgggac | gcaaagcagc | caccttcgtc | 180 |
| gctaacatcg | ccgatcgcgc | gcaggtgtac | gccgccattg | atgaagcgga | aaaacagctg | 240 |
| ggcggctttg | atattatcgt | gaacaacgcc | gggatcgccc | aggttcaggc | gctggccgat | 300 |
| gtgacgcctg | aagaagtgga | ccgcatcatg | cgcatcaacg | ttcagggtac | cctgtggggt | 360 |
| attcaggcgg | cggcgaaaaa | attcatcgat | cgtcagcaga | aagggaaaat | catcaacgcc | 420 |
| tgctctatcg | ccggtcatga | tggtttcgcg | ctgctgggcg | tttattccgc | caccaaattt | 480 |
| gccgtacgcg | ccctgacgca | ggcggcggcg | aaggagtatg | ccagccgcgg | cattacggtt | 540 |
| aatgcctact | gtccggggat | tgtgggaacc | gggatgtgga | ccgaaatcga | taagcgcttt | 600 |
| gcggaaatta | ccggtgcgcc | ggtgggcgaa | acttataaaa | aatacgttga | aggcatcgcc | 660 |
| cttggccgcg | ccgaaacgcc | ggacgatgtg | gcaagcctgg | tctcttatct | ggcaggcccg | 720 |
| gattccgatt | atgttaccgg | tcagtcgatt | ctgatcgatg | gcggtattgt | ttaccgt | 777 |

<210> SEQ ID NO 13
<211> LENGTH: 621
<212> TYPE: DNA
<213> ORGANISM: Artificial
<220> FEATURE:
<223> OTHER INFORMATION: a homologous region 1 of darKo

<400> SEQUENCE: 13

| | | | | | | |
|---|---|---|---|---|---|---|
| ggaggtcggc | cggaagctcg | ccttgcagca | gctgcagaaa | cgacgggctc | cacccctgcc | 60 |
| acaagggccg | cagcgcctcc | tgcagatagc | gtataaacag | tagcggcgcg | ttgtcatcct | 120 |
| cttcaaggct | cagccaggcc | agcgcatccc | cttgtcgaag | gcggtgtcga | taccactgcg | 180 |
| ccagcagggt | ggttttgcca | aatccggcgg | gcgcgcgcac | cagggttaaa | cggcgggaga | 240 |
| cggcggcgtc | gaggcgctgt | agcaggcgct | cccgcgatag | cagactttcc | ggcgtacggg | 300 |
| gcggcgtaaa | gcgcgtggag | ataagcggca | gcgtccccgt | gaagcgtaaa | ggttcctgat | 360 |
| gaacaagcgc | tgccagcgca | tcatccgccg | aggataaaaa | ggccatacca | cgattactcc | 420 |
| ttaatccagt | ccgtacgctc | attatccccc | ccatcagggg | ggtaggccac | gcttatcgcg | 480 |
| cccgatagag | tagtgccatt | cgccgcagcg | gctacgacga | catcggccgc | gggcctccct | 540 |
| agtttattaa | tcagtacaag | gtgagtacag | acatggctat | cgaaaataaa | gttgcgaccg | 600 |
| gtcagtcgat | tctgatcgat | g | | | | 621 |

<210> SEQ ID NO 14
<211> LENGTH: 34
<212> TYPE: DNA
<213> ORGANISM: Artificial
<220> FEATURE:
<223> OTHER INFORMATION: a primer for PCR amplification of the sequence of SEQ ID NO: 13

<400> SEQUENCE: 14

| | | | |
|---|---|---|---|
| tctagaggat | ccggaggtcg | gccggaagct cgcc | 34 |

```
<210> SEQ ID NO 15
<211> LENGTH: 52
<212> TYPE: DNA
<213> ORGANISM: Artificial
<220> FEATURE:
<223> OTHER INFORMATION: a primer for PCR amplification of the sequence
      of SEQ ID NO: 13

<400> SEQUENCE: 15
catcgatcag aatcgactga ccggtcgcaa ctttatttc gatagccatg tc            52

<210> SEQ ID NO 16
<211> LENGTH: 608
<212> TYPE: DNA
<213> ORGANISM: Artificial
<220> FEATURE:
<223> OTHER INFORMATION: a homologous region 2 of darKo

<400> SEQUENCE: 16
gacatggcta tcgaaaataa agttgcgacc ggtcagtcga ttctgatcga tggcggtatt    60
gtttaccgtt aagggataaa cccggcgcag aacgcgccgg ttttttgcgg ggttacgcgt   120
tagccgcggg ctcctgcggc ttgtcgctac gggtgttttc cagcatccgg cgaaccggaa   180
caatcagcag gcacagcacc gcggcgcaga tcagcagcgc aatagagcag cgtgcgaaca   240
ggtcgggcag catatccagc tgatcggcct tcacgtgacc gccaatcaga cccgccgcca   300
ggttccccag ggcgctggcg cagaaccaca gccccatcat ctggccgcgc attctttccg   360
gcgccagcag cgtcatggtc gcgaggccaa tcgggctgag gcacagctcg cccagcgtca   420
gcatcagaat actgcccacc agccacatcg gcgagacgcc cgcgccgttg ttgctcagga   480
cgttttgcgc cgccagcatc atcaggccaa agcccgccgc cgcgcataaa ataccgataa   540
caaacttggt gatgctgctc ggacgcacgt ttttacgcgc cagcgcaggc cacgcccagc   600
taaatacc                                                           608

<210> SEQ ID NO 17
<211> LENGTH: 52
<212> TYPE: DNA
<213> ORGANISM: Artificial
<220> FEATURE:
<223> OTHER INFORMATION: a primer for PCR amplification of the sequence
      of SEQ ID NO: 16

<400> SEQUENCE: 17
gacatggcta tcgaaaataa agttgcgacc ggtcagtcga ttctgatcga tg            52

<210> SEQ ID NO 18
<211> LENGTH: 35
<212> TYPE: DNA
<213> ORGANISM: Artificial
<220> FEATURE:
<223> OTHER INFORMATION: a primer for PCR amplification of the sequence
      of SEQ ID NO: 16

<400> SEQUENCE: 18
atcgcggccg cggtatttag ctgggcgtgg cctgc                               35

<210> SEQ ID NO 19
<211> LENGTH: 1177
<212> TYPE: DNA
<213> ORGANISM: Artificial
<220> FEATURE:
<223> OTHER INFORMATION: a DNA fragment in which a homologous region 1
      (SEQ ID NO: 13) and a homologous region 2 (SEQ ID NO: 16) of darKo
      are ligated
```

<400> SEQUENCE: 19

```
ggaggtcggc cggaagctcg ccttgcagca gctgcagaaa cgacgggctc caccccctgcc      60
acaagggccg cagcgcctcc tgcagatagc gtataaacag tagcggcgcg ttgtcatcct     120
cttcaaggct cagccaggcc agcgcatccc cttgtcgaag gcggtgtcga taccactgcg     180
ccagcagggt ggttttgcca atccggcgg gcgcgcgcac cagggttaaa cggcgggaga     240
cggcggcgtc gaggcgctgt agcaggcgct cccgcgatag cagactttcc ggcgtacggg     300
gcggcgtaaa gcgcgtggag ataagcggca gcgtccccgt gaagcgtaaa ggttcctgat     360
gaacaagcgc tgccagcgca tcatccgccg aggataaaaa ggccatacca cgattactcc     420
ttaatccagt ccgtacgctc attatccccc ccatcagggg ggtaggccac gcttatcgcg     480
cccgatagag tagtgccatt cgccgcagcg gctacgacga catcggccgc gggcctccct     540
agtttattaa tcagtacaag gtgagtacag acatggctat cgaaaataaa gttgcgaccg     600
gtcagtcgat tctgatcgat ggcggtattg tttaccgtta agggataaac ccggcgcaga     660
acgcgccggg tttttgcggg gttacgcgtt agccgcgggc tcctgcggct tgtcgctacg     720
ggtgttttcc agcatccggc gaaccggaac aatcagcagg cacagcaccg cggcgcagat     780
cagcagcgca atagagcagc gtgcgaacag gtcgggcagc atatccagct gatcggcctt     840
cacgtgaccg ccaatcagac ccgccgccag gttccccagg gcgctggcgc agaaccacag     900
ccccatcatc tggccgcgca ttctttccgg cgccagcagc gtcatggtcg cgaggccaat     960
cgggctgagg cacagctcgc ccagcgtcag catcagaata ctgcccacca gccacatcgg    1020
cgagacgccc gcgccgttgt tgctcaggac gttttgcgcc gccagcatca tcaggccaaa    1080
gcccgccgcc gcgcataaaa taccgataac aaacttggtg atgctgctcg gacgcacgtt    1140
tttacgcgcc agcgcaggcc acgcccagct aaatacc                              1177
```

<210> SEQ ID NO 20
<211> LENGTH: 350
<212> TYPE: PRT
<213> ORGANISM: Paenibacillus polymyxa

<400> SEQUENCE: 20

```
Met Gln Ala Leu Arg Trp His Gly Val Lys Asp Leu Arg Leu Glu Asn
1               5                   10                  15
Ile Glu Gln Pro Ala Ala Leu Pro Gly Lys Val Lys Ile Lys Val Glu
            20                  25                  30
Trp Cys Gly Ile Cys Gly Ser Asp Leu His Glu Tyr Val Ala Gly Pro
        35                  40                  45
Ile Phe Ile Pro Glu Asn Ala Gln His Pro Leu Thr Gly Glu Lys Ala
    50                  55                  60
Pro Ile Val Met Gly His Glu Phe Ser Gly Gln Val Val Glu Ile Gly
65                  70                  75                  80
Glu Gly Val Thr Lys Ile Gln Val Gly Asp Arg Val Val Val Glu Pro
                85                  90                  95
Val Phe Ala Cys Gly Glu Cys Asp Ala Cys Arg Gln Gly Lys Tyr Asn
            100                 105                 110
Leu Cys Asp Lys Met Gly Phe Leu Gly Leu Ala Gly Gly Gly Gly Gly
        115                 120                 125
Phe Ser Glu Tyr Val Ala Ala Asp Glu His Met Val His Lys Ile Pro
    130                 135                 140
Glu Ser Val Ser Phe Glu Gln Gly Ala Leu Val Glu Pro Ser Ala Val
145                 150                 155                 160
```

| Ala | Leu | Tyr | Ala | Val | Arg | Gln | Ser | Gln | Leu | Lys | Val | Gly | Asp | Lys | Ala |
|---|---|---|---|---|---|---|---|---|---|---|---|---|---|---|---|
| | | | | 165 | | | | 170 | | | | | 175 | | |

| Val | Val | Phe | Gly | Ala | Gly | Pro | Ile | Gly | Leu | Leu | Val | Ile | Glu | Ala | Leu |
|---|---|---|---|---|---|---|---|---|---|---|---|---|---|---|---|
| 180 | | | | | | | 185 | | | | | 190 | | | |

| Lys | Ala | Ser | Gly | Ala | Ser | Glu | Ile | Tyr | Ala | Val | Glu | Leu | Ser | Glu | Glu |
|---|---|---|---|---|---|---|---|---|---|---|---|---|---|---|---|
| | | 195 | | | | | 200 | | | | | 205 | | | |

| Arg | Lys | Ala | Lys | Ala | Glu | Glu | Leu | Gly | Ala | Ile | Val | Leu | Asp | Pro | Lys |
|---|---|---|---|---|---|---|---|---|---|---|---|---|---|---|---|
| | 210 | | | | | 215 | | | | | 220 | | | | |

| Thr | Tyr | Asp | Val | Val | Glu | Leu | His | Lys | Arg | Thr | Asn | Gly | Gly | Val |
|---|---|---|---|---|---|---|---|---|---|---|---|---|---|---|
| 225 | | | | | 230 | | | | | 235 | | | | 240 |

| Asp | Val | Ala | Tyr | Glu | Val | Thr | Gly | Val | Pro | Pro | Val | Leu | Thr | Gln | Ala |
|---|---|---|---|---|---|---|---|---|---|---|---|---|---|---|---|
| | | | | 245 | | | | | 250 | | | | | 255 | |

| Ile | Glu | Ser | Thr | Lys | Ile | Ser | Gly | Gln | Ile | Met | Ile | Val | Ser | Ile | Phe |
|---|---|---|---|---|---|---|---|---|---|---|---|---|---|---|---|
| | | | 260 | | | | | 265 | | | | | 270 | | |

| Glu | Lys | Glu | Ala | Pro | Ile | Lys | Pro | Asn | Asn | Ile | Val | Met | Lys | Glu | Arg |
|---|---|---|---|---|---|---|---|---|---|---|---|---|---|---|---|
| | | 275 | | | | | 280 | | | | | 285 | | | |

| Asn | Leu | Thr | Gly | Ile | Ile | Gly | Tyr | Arg | Asp | Val | Phe | Pro | Ala | Val | Ile |
|---|---|---|---|---|---|---|---|---|---|---|---|---|---|---|---|
| | 290 | | | | | 295 | | | | | 300 | | | | |

| Ser | Leu | Met | Glu | Lys | Gly | Tyr | Phe | Pro | Ala | Asp | Lys | Leu | Val | Thr | Lys |
|---|---|---|---|---|---|---|---|---|---|---|---|---|---|---|---|
| 305 | | | | | 310 | | | | | 315 | | | | | 320 |

| Arg | Ile | Lys | Leu | Glu | Glu | Val | Ile | Glu | Gln | Gly | Phe | Glu | Gly | Leu | Leu |
|---|---|---|---|---|---|---|---|---|---|---|---|---|---|---|---|
| | | | | 325 | | | | | 330 | | | | | 335 | |

| Lys | Glu | Lys | Asn | Gln | Val | Lys | Ile | Leu | Val | Ser | Pro | Lys | Ala |
|---|---|---|---|---|---|---|---|---|---|---|---|---|---|
| | | | 340 | | | | | 345 | | | | 350 | |

<210> SEQ ID NO 21
<211> LENGTH: 1050
<212> TYPE: DNA
<213> ORGANISM: Paenibacillus polymyxa

<400> SEQUENCE: 21

```
atgcaagcat tgagatggca tggagtaaaa gatttacgtt tggaaaacat tgagcaaccc      60
gctgctcttc caggaaaagt aaaaatcaaa gtagaatggt gtggcatttg cggaagtgat     120
cttcacgaat atgtagcagg accgatcttc attcctgaaa acgctcagca tccactgact     180
ggcgaaaaag ctccgattgt gatgggacat gaattttctg acaagtcgt tgaaatcggt      240
gaaggtgtaa ctaaaattca ggttggcgac cgtgtagtcg tagaaccggt ttttgcatgt     300
ggagaatgtg atgcatgtag acaaggcaaa tataaccttt gcgataaaat gggcttcctc     360
ggtttggcag gcggcggcgg tggatttttct gaatatgtcg cagctgacga gcacatggtt    420
cacaaaattc agaaagcgt atccttcgag caaggcgctt tggtagagcc ttcggccgtt      480
gctttgtacg ctgtacgtca aagccaactg aaagtcggcg acaaagctgt cgtgtttggc     540
gctggtccta tcggattgct ggttattgaa gcgttgaaag cttcgggcgc atctgagatt     600
tatgcagtag agctttccga ggagcgtaaa gctaaagctg aagagctggg tgctattgtg     660
cttgatccta aaacttatga tgttgtggaa gaactgcaca acggaccaa cggtggcgta      720
gatgtagcct atgaagtcac tggagtacct cctgtgctga ctcaagcgat tgaatccact     780
aaaattagcg gacaaatcat gatcgtcagc atttttgaaa aagaagctcc aatcaaaccg     840
aacaatatcg ttatgaagga acgcaatctg actggtatta tcggctaccg tgatgtattc     900
ccggctgtca tcagcttgat ggaaaaaggg tatttccctg ctgacaagct tgtgaccaaa     960
cgtattaagc tcgaagaagt aatcgagcaa ggttttgaag gtctcctgaa agaaaaaaat    1020
caggttaaaa tcctggtatc tccgaaagcc                                      1050
```

<210> SEQ ID NO 22
<211> LENGTH: 1500
<212> TYPE: DNA
<213> ORGANISM: Artificial
<220> FEATURE:
<223> OTHER INFORMATION: a homologous region 1 of budCKo

<400> SEQUENCE: 22

| | |
|---|---|
| ccgcatcacc ggcaaagcgg gcgtcgcgct ggtcacgtcc ggaccgggct gctctaacct | 60 |
| gattaccggg atggcaacgg ccaatagcga aggcgacccg gtggtggcgc tgggcggcgc | 120 |
| ggtaaaacgc gccgacaagg ccaaacaggt gcaccagagt atggatacgg tgacgatgtt | 180 |
| tagcccggtg accaaatact cggtggaagt caccgcgccg aagcgctgg cggaagttgt | 240 |
| ctccaacgcg tttcgtgcag ccgagcaggg acgccccggc agcgccttcg tcagcctgcc | 300 |
| gcaggacgtg gtcgacgggc cggtccacgc cagggttctg cccgccggcg atgcgccgca | 360 |
| gaccggcgcg gcgccggacg acgccattgc gcgagtcgcg aagatgattg ccggcgcgaa | 420 |
| aaatccgata tttctgctcg gcctgatggc cagccgacg gaaaacagcg cggcgctgcg | 480 |
| cgaattgctg aaaaaaagtc atatcccggt gaccagcacc tatcaggccg ccggcgcagt | 540 |
| caatcaggat cactttaccc gcttcgccgg acgggttggt ctgttcaaca accaggcagg | 600 |
| ggatcgactc ctgcatctcg ccgacctggt catctgcatc ggctatagtc cggtggagta | 660 |
| cgagccggcc atgtggaata acggtaacgc cacgctggta catatcgacg tgctgccgc | 720 |
| ttacgaagag cgtaattata ccccggacgt cgagctggtc ggcaatatcg ccgccaccct | 780 |
| gaacaaactg tctcaacgca tcgaccacca gctggtgctc tcgccgcagg ccgccgagat | 840 |
| ccttgtcgac cgccagcatc agcgggagct cctcgaccgc cgcggtgcgc acctgaacca | 900 |
| gttcgcgctt catccgctgc gcatcgttcg cgccatgcag gacatcgtca atagcgatgt | 960 |
| caccctgacc gtcgatatgg ggagctttca tatctggatc gcccgctatc tctacagctt | 1020 |
| tcgcgcccgt caggtcatga tttccaacgg tcaacagacc atgggcgtgg cgctgccgtg | 1080 |
| ggcgattggc gcctggctgg tcaatccgca gcgcaaagtg gtttccgttt ccggcgacgg | 1140 |
| cggtttcctg cagtccagca tggagctgga gaccgctgta cggctgaaag cgaacgtcct | 1200 |
| gcatatcatc tgggtcgata acggctacaa catggtggcg attcaggagg agaaaaaata | 1260 |
| ccagcggctc tccggcgttg agttcggccc ggtggatttt aaagtctacg ccgaagcctt | 1320 |
| cggcgccaaa gggtttgcgg tagagagcgc cgaagcccttt gagccgacgc tgcgggcggc | 1380 |
| gatggacgtc gacggccccg ccgtcgtagc catccccgtg gattaccgcg ataacccgct | 1440 |
| gctgatgggc cagctccatc tcagtcaact actttgagtc actacagaag gaatctatca | 1500 |

<210> SEQ ID NO 23
<211> LENGTH: 28
<212> TYPE: DNA
<213> ORGANISM: Artificial
<220> FEATURE:
<223> OTHER INFORMATION: a primer for PCR amplification of the sequence
    of SEQ ID NO: 22

<400> SEQUENCE: 23

| | |
|---|---|
| ggatccccgc atcaccggca aagcgggc | 28 |

<210> SEQ ID NO 24
<211> LENGTH: 48
<212> TYPE: DNA
<213> ORGANISM: Artificial

```
<220> FEATURE:
<223> OTHER INFORMATION: a primer for PCR amplification of the sequence
      of SEQ ID NO: 22

<400> SEQUENCE: 24
ctccatgcca tctcaatgct tgcattgata gattccttct gtagtgac                    48

<210> SEQ ID NO 25
<211> LENGTH: 47
<212> TYPE: DNA
<213> ORGANISM: Artificial
<220> FEATURE:
<223> OTHER INFORMATION: a primer for PCR amplification of bdhPp (SEQ ID
      NO: 21)

<400> SEQUENCE: 25
tcactacaga aggaatctat caatgcaagc attgagatgg catggag                     47

<210> SEQ ID NO 26
<211> LENGTH: 50
<212> TYPE: DNA
<213> ORGANISM: Artificial
<220> FEATURE:
<223> OTHER INFORMATION: a primer for PCR amplification of bdhPp (SEQ ID
      NO: 21)

<400> SEQUENCE: 26
caaaccatgt cagagcttat ttattattag gctttcggag ataccaggat                  50

<210> SEQ ID NO 27
<211> LENGTH: 1500
<212> TYPE: DNA
<213> ORGANISM: Artificial
<220> FEATURE:
<223> OTHER INFORMATION: a homologous region 2 of budCKo

<400> SEQUENCE: 27
taataaataa gctctgacat ggtttgcccc ggcgtcaccg ccggggcttt tttatttcaa        60
cctttaggga agatccacag gtcgctgacg ggcaatgtca gatggcaacg ctcggcatcg       120
cgcagcgcgc tgccgtaggc gcgtatggcg aaatcatcgc cttcagtgcg aaacagatac       180
tcccagcggt cgccgaggta catgctggtc aacagcggca gcgccagcat gttctcttca       240
ggcgcggaag cgatgcgcaa acgctcaacg cggatcaccg ccgtcgcctc ttcccccacg       300
ctaacccctt cccccgccat tccccatagc gcccagctgg cccctcaat gcgcgcccga       360 ccgttctcca gcgcgctaac ggtgccatgc aggcgattat tactgcccat aaactcggcg       420
gcaaacagcg ttttcgggct gccgtacatc tcctgcgggg ttccctgctg ctcgatcacg       480
ccgttgttaa gcagcagaat gcgatcggaa atcgccatcg cctcattctg atcgtgggtg       540
accatcagcg ccgaaagccc cagcttgacg atcagctcgc gcaaaaagac ccgcgcttct       600
tcccgcagct tggcgtccag attcgacagc ggttcatcca gcaggatcac cggcgggttg       660
taaaccagcg ccctgccgat ggccacgcgc tgctgctgtc ctccggagag ctgatgcgga       720
tggcgactgc caagatgccc cagcccaagc tgttcaagta cggtctggac ccgttgcttg       780
atctccgcgg cggcaacctt acgcagcttc agcgggtaag cgacgttttc aaacaccgtt       840
ttatgcggcc acagcgcata ggactgaaac accagaccca ggttacgctc ctcggccgga       900
atttcgctac gcgggttgcc gtcatagacg cgggatttc caatggtaat aatgccgccg       960
gtcggcttct ccagcccggc gaccgccgc agcagcgtgg ttttccgct gcccgatggc      1020 ccgagcagcg acaccacctc tccccgcttc agttccatgg acacgcccctt cagtaccgga     1080
```

```
ttatcgccat aggtcagatg caggtttcct accgataatt caatcatgta atttcactcc    1140
aaagcgcagg gcgatacccc gaccgacgac caccagcagg atattaataa aggagagcgc    1200
ggcgacgata tcgatagccc ccgccgccca cagcgagacc agcatcgaac caatcgtttc    1260
ggttccgggc gaaagcagat agaccccggt ggagtattcg cgctcgaaga taagaaacat    1320
cagcagccag gagccgatta agccgtagcg cgacagcggc accgtaacgt gacgggtaat    1380
ctgcccgcgc gatgcgccgg tactgcgcgc ggcctcttcc aactccggcg ctacctgcag    1440
cagcgtcgag gagatcagcc gcaggccgta agccatccac accacggtat aggccagcca    1500
```

<210> SEQ ID NO 28
<211> LENGTH: 50
<212> TYPE: DNA
<213> ORGANISM: Artificial
<220> FEATURE:
<223> OTHER INFORMATION: a primer for PCR amplification of budCKo

<400> SEQUENCE: 28

```
atcctggtat ctccgaaagc ctaataataa ataagctctg acatggtttg                50
```

<210> SEQ ID NO 29
<211> LENGTH: 31
<212> TYPE: DNA
<213> ORGANISM: Artificial
<220> FEATURE:
<223> OTHER INFORMATION: a primer for PCR amplification of budCKo

<400> SEQUENCE: 29

```
gcggccgctg gctggcctat accgtggtgt g                                    31
```

<210> SEQ ID NO 30
<211> LENGTH: 4053
<212> TYPE: DNA
<213> ORGANISM: Artificial
<220> FEATURE:
<223> OTHER INFORMATION: a DNA fragment in which a homologous region 1
    (SEQ ID NO: 22) of budCKo, bdhPp (SEQ ID NO: 21), and a homologous
    region 2 (SEQ ID NO: 27) of budCKo are ligated

<400> SEQUENCE: 30

```
ccgcatcacc ggcaaagcgg gcgtcgcgct ggtcacgtcc ggaccgggct gctctaacct     60
gattaccggg atggcaacgg ccaatagcga aggcgaccg gtggtggcgc tgggcggcgc    120
ggtaaaacgc gccgacaagg ccaaacaggt gcaccagagt atggatacgg tgacgatgtt    180
tagcccggtg accaaatact cggtggaagt caccgcgccg aagcgctgg cggaagttgt    240 ctccaacgcg tttcgtgcag ccgagcaggg acgccccggc agcgccttcg tcagcctgcc    300
gcaggacgtg gtcgacgggc cggtccacgc caggggtctg cccgccggcg atgcgccgca    360
gaccggcgcg gcgccggacg acgccattgc gcgagtcgcg aagatgattg ccggcgcgaa    420
aaatccgata tttctgctcg gcctgatggc cagccagacg gaaaacagcg cggcgctgcg    480
cgaattgctg aaaaaaagtc atatcccggt gaccagcacc tatcaggccg ccggcgcagt    540
caatcaggat cactttaccc gcttcgccgg acgggttggt ctgttcaaca accaggcagg    600
ggatcgactc ctgcatctcg ccgacctggt catctgcatc ggctatagtc cggtggagta    660
cgagccggcc atgtggaata acggtaacgc cacgctggta catatcgacg tgctgcccgc    720
ttacgaagag cgtaattata cccggacgt cgagctggtc ggcaatatcg ccgccaccct    780
gaacaaactg tctcaacgca tcgaccacca gctggtgctc tcgccgcagg ccgccgagat    840
ccttgtcgac cgccagcatc agcgggagct cctcgaccgc gcggtgcgc acctgaacca    900
```

```
gttcgcgctt catccgctgc gcatcgttcg cgccatgcag gacatcgtca atagcgatgt      960
caccctgacc gtcgatatgg ggagctttca tatctggatc gcccgctatc tctacagctt     1020
tcgcgcccgt caggtcatga tttccaacgg tcaacagacc atgggcgtgg cgctgccgtg     1080
ggcgattggc gcctggctgg tcaatccgca gcgcaaagtg gtttccgttt ccggcgacgg     1140
cggtttcctg cagtccagca tggagctgga gaccgctgta cggctgaaag cgaacgtcct     1200
gcatatcatc tgggtcgata acggctacaa catggtggcg attcaggagg agaaaaaata     1260
ccagcggctc tccggcgttg agttcggccc ggtggatttt aaagtctacg ccgaagcctt     1320
cggcgccaaa gggtttgcgg tagagagcgc cgaagccctt gagccgacgc tgcgggcggc     1380
gatggacgtc gacggccccg ccgtcgtagc catccccgtg gattaccgcg ataacccgct     1440
gctgatgggc cagctccatc tcagtcaact actttgagtc actacagaag gaatctatca     1500
atgcaagcat tgagatggca tggagtaaaa gatttacgtt tggaaaacat tgagcaaccc     1560
gctgctcttc caggaaaagt aaaaatcaaa gtagaatggt gtggcatttg cggaagtgat     1620
cttcacgaat atgtagcagg accgatcttc attcctgaaa acgctcagca tccactgact     1680
ggcgaaaaag ctccgattgt gatgggacat gaattttctg gacaagtcgt tgaaatcggt     1740
gaaggtgtaa ctaaaattca ggttggcgac cgtgtagtcg tagaaccggt ttttgcatgt     1800
ggagaatgtg atgcatgtag acaaggcaaa tataaccttt gcgataaaat gggcttcctc     1860
ggtttggcag gcggcggcgg tggatttttct gaatatgtcg cagctgacga gcacatggtt     1920
cacaaaattc cagaaagcgt atccttcgag caaggcgctt tggtagagcc ttcggccgtt     1980
gctttgtacg ctgtacgtca aagccaactg aaagtcggcg acaaagctgt cgtgtttggc     2040
gctggtccta tcggattgct ggttattgaa gcgttgaaag cttcgggcgc atctgagatt     2100
tatgcagtag agctttccga ggagcgtaaa gctaaagctg aagagctggg tgctattgtg     2160
cttgatccta aaacttatga tgttgtggaa gaactgcaca aacggaccaa cggtggcgta     2220
gatgtagcct atgaagtcac tggagtacct cctgtgctga ctcaagcgat tgaatccact     2280
aaaattagcg gacaaatcat gatcgtcagc atttttgaaa aagaagctcc aatcaaaccg     2340
aacaatatcg ttatgaagga acgcaatctg actggtatta tcggctaccg tgatgtattc     2400
ccggctgtca tcagcttgat ggaaaaaggg tatttccctg ctgacaagct tgtgaccaaa     2460
cgtattaagc tcgaagaagt aatcgagcaa ggttttgaag gtctcctgaa agaaaaaaat     2520
caggttaaaa tcctggtatc tccgaaagcc taataataaa taagctctga catggtttgc     2580
cccggcgtca ccgccgggc ttttttattt caacctttag ggaagatcca caggtcgctg     2640
acgggcaatg tcagatggca acgctcggca tcgcgcagcg cgctgccgta ggcgcgtatg     2700
gcgaaatcat cgccttcagt gcgaaacaga tactcccagc ggtcgccgag gtacatgctg     2760
gtcaacagcg gcagcgccag catgttctct tcaggcgcgg aagcgatgcg caaacgctca     2820
acgcggatca ccgccgtcgc ctcttccccc acgctaaccc cttccccgc cattccccat     2880
agcgcccagc tggcccctc aatgcgcgcc cgaccgttct ccagcgcgct aacggtgcca     2940
tgcaggcgat tattactgcc cataaactcg gcggcaaaca gcgttttcgg gctgccgtac     3000
atctcctgcg gggttccctg ctgctcgatc acgccgttgt taagcagcag aatgcgatcg     3060
gaaatcgcca tcgcctcatt ctgatcgtgg gtgaccatca gcgccgaaag ccccagcttg     3120
acgatcagct cgcgcaaaaa gaccgcgcct tcttcccgca gcttggcgtc cagattcgac     3180
agcggttcat ccagcaggat caccggcggg ttgtaaacca gcgccctgcc gatggccacg     3240
cgctgctgct gtcctccgga gagctgatgc ggatggcgac tgccaagatg ccccagccca     3300
```

| | |
|---|---|
| agctgttcaa gtacggtctg gacccgttgc ttgatctccg cggcggcaac cttacgcagc | 3360 |
| ttcagcgggt aagcgacgtt ttcaaacacc gttttatgcg gccacagcgc ataggactga | 3420 |
| aacaccagac ccaggttacg ctcctcggcc ggaatttcgc tacgcgggtt gccgtcatag | 3480 |
| acgcgggatt ttccaatggt aataatgccg ccggtcggct tctccagccc ggcgaccgcc | 3540 |
| cgcagcagcg tggttttttcc gctgcccgat ggcccgagca gcgacaccac ctctccccgc | 3600 |
| ttcagttcca tggacacgcc cttcagtacc ggattatcgc cataggtcag atgcaggttt | 3660 |
| tctaccgata attcaatcat gtaatttcac tccaaagcgc agggcgatac ccagaccgac | 3720 |
| gaccaccagc aggatattaa taaaggagag cgcggcgacg atatcgatag ccccgccgc | 3780 |
| ccacagcgag accagcatcg aaccaatcgt ttcggttccg ggcgaaagca gatagacccc | 3840 |
| ggtggagtat tcgcgctcga agataagaaa catcagcagc caggagccga ttaagccgta | 3900 |
| gcgcgacagc ggcaccgtaa cgtgacgggt aatctgcccg cgcgatgcgc cggtactgcg | 3960 |
| cgcggcctct tccaactccg cgctacctg cagcagcgtc gaggagatca gccgcaggcc | 4020 |
| gtaagccatc cacaccacgg tataggccag cca | 4053 |

<210> SEQ ID NO 31
<211> LENGTH: 1099
<212> TYPE: DNA
<213> ORGANISM: Artificial
<220> FEATURE:
<223> OTHER INFORMATION: a homologous region 1 of darKo

<400> SEQUENCE: 31

| | |
|---|---|
| gccgcagacg acgtcgcaca gcgccggatg caggcgatta agcatcgagg tctgcagaag | 60 |
| gaagtcgagc acctctggcg gcagcggcgc gaaaatcacc tcatccagat agcgggagat | 120 |
| tgaccgcgag ccggcgctgt gacccatcgc cgtggaggcg tccgcagaga gcgcggccat | 180 |
| tttcattccc gcgatccacc cttccgtgag cgcgattagc cgcgggatcg cctgcggatc | 240 |
| cagccccgat gcgccggaga accaggcgcg ggcttcgctg ggggtaaagc gcagctcggg | 300 |
| gtcgtacacc tccagcagct gatcctgcat atgcagacgg ctgagggcta agacggctg | 360 |
| actgcggcta ccgataatca ggtgcagcgc cggcggcgca tggtccagca gccagctcat | 420 |
| tccctgatga atcgccggat cgctgatgca ttgatagtcg tcgaggatca gatacagcgg | 480 |
| gtgcgggcac tgattaagct gattaacgag ttcagcaaag aacaggggga ggtcggccgg | 540 |
| aagctcgcct tgcagcagct gcagaaacga cgggctccac ccctgccaca agggccgcag | 600 |
| cgcctcctgc agatagcgta taaacagtag cggcgcgttg tcatcctctt caaggctcag | 660 |
| ccaggccagc gcatcccctt gtcgaaggcg gtgtcgatac cactgcgcca gcagggtggt | 720 |
| tttgccaaat ccggcgggcg cgcgcaccag ggttaaacgg cgggagacgg cggcgtcgag | 780 |
| gcgctgtagc aggcgctccc gcgatagcag actttccggc gtacggggcg gcgtaaagcg | 840 |
| cgtggagata gcggcagcg tccccgtgaa gcgtaaaggt tcctgatgaa caagcgctgc | 900 |
| cagcgcatca tccgccgagg ataaaaaggc cataccacga ttactcctta atccagtccg | 960 |
| tacgctcatt atccccccca tcagggggt aggccacgct tatcgcgccc gatagagtag | 1020 |
| tgccattcgc cgcagcggct acgacgacat cggccgcggg cctccctagt ttattaatca | 1080 |
| gtacaaggtg agtacagac | 1099 |

<210> SEQ ID NO 32
<211> LENGTH: 33
<212> TYPE: DNA
<213> ORGANISM: Artificial

<220> FEATURE:
<223> OTHER INFORMATION: a primer for PCR amplification of darKo

<400> SEQUENCE: 32
tcgactctag agccgcagac gacgtcgcac agc        33

<210> SEQ ID NO 33
<211> LENGTH: 43
<212> TYPE: DNA
<213> ORGANISM: Artificial
<220> FEATURE:
<223> OTHER INFORMATION: a primer for PCR amplification of darKo

<400> SEQUENCE: 33
catgccatct caatgcttgc atgtctgtac tcaccttgta ctg        43

<210> SEQ ID NO 34
<211> LENGTH: 43
<212> TYPE: DNA
<213> ORGANISM: Artificial
<220> FEATURE:
<223> OTHER INFORMATION: a primer for PCR amplification of bdhPp (SEQ ID
    NO: 21)

<400> SEQUENCE: 34
cagtacaagg tgagtacaga catgcaagca ttgagatggc atg        43

<210> SEQ ID NO 35
<211> LENGTH: 40
<212> TYPE: DNA
<213> ORGANISM: Artificial
<220> FEATURE:
<223> OTHER INFORMATION: a primer for PCR amplification of bdhPp (SEQ ID
    NO: 21)

<400> SEQUENCE: 35
ctgcgccggg tttatccctt aggctttcgg agataccagg        40

<210> SEQ ID NO 36
<211> LENGTH: 1500
<212> TYPE: DNA
<213> ORGANISM: Artificial
<220> FEATURE:
<223> OTHER INFORMATION: a homologous region 2 of darKo

<400> SEQUENCE: 36
gggataaacc cggcgcagaa cgcgccgggt ttttgcgggg ttacgcgtta gccgcgggct        60
cctgcggctt gtcgctacgg gtgttttcca gcatccggcg aaccggaaca atcagcaggc        120
acagcaccgc ggcgcagatc agcagcgcaa tagagcagcg tgcgaacagg tcggcagca        180 tatccagctg atcggccttc acgtgaccgc caatcagacc cgccgccagg ttccccaggg        240
cgctggcgca gaaccacagc ccatcatct ggccgcgcat tctttccggc gccagcagcg        300
tcatggtcgc gaggccaatc gggctgaggc acagctcgcc cagcgtcagc atcagaatac        360
tgcccaccag ccacatcggc gagacgcccg cgccgttgtt gctcaggacg ttttgcgccg        420
ccagcatcat caggccaaag cccgccgccg cgcataaaat accgataaca aacttggtga        480
tgctgctcgg acgcacgttt ttacgcgcca gcgcaggcca cgcccagcta aataccggcg        540
ccagcagaat aataaacagg gcgttaatcg actggaacca caccgccggg atctcgaagg        600
agccgagcat acgcgttggta tagtcgttag cgaacaggtt aaacgaggtc ggtttctgct        660
caaacgccga ccagaaaaag gcggcagaga tcagcaggat aaagcatacc agcaggcggg        720

```
cgcgctcttt gcggctcaat ccggcgaaga cgaacaggta gataaaatag agtaccaccg    780
acgccgcaat cacgtagacc agtacgctgg cgaccgccac cgggttaatc acgataacgc    840
cctgggcaat caaggcgatg ataaccgcca cgcccaccgt tagcgccagc aaccatgcgc    900
cgacgccatt tcgtttcact accgggctgt tccaggtgga atcgaggccg acttcactgt    960
cgtagcgttt catcgccggg acggcaaaaa cgcggaagat aatcagcgcg accagcatcc   1020
cgatgccgcc gatgccgaag ccccagtgcc agccgtggga tttaatcagc cagccggaga   1080
tcagcggggc gataaacgac cccatgttga tgcccatata aaacagcgag aagccgccat   1140
cgcggcgcgc atcgcctttt ttgtagaggg taccgaccat caccgaaata caggttttaa   1200
acaggccgga accgagcacg ataaacatca ggccaataaa gaacaggcta tcgcccatca   1260
ccgccgacag ggcgatggag agatggccca gagcgatcag tatcgaaccg taccagaccg   1320
ccttttgttg cccgagccag ttatcagcca gccagccgcc cggcagcgcg gcaagataca   1380
tggtcccggc aaagatcccg acaatggccg acgcgttctc gcgcgccagc cccatcccac   1440
cgtcatagac ggtggccgcc ataaacagga tcagtaacgg acgaataccg taaaacgaga   1500
```

<210> SEQ ID NO 37
<211> LENGTH: 40
<212> TYPE: DNA
<213> ORGANISM: Artificial
<220> FEATURE:
<223> OTHER INFORMATION: a primer for PCR amplification of darKo

<400> SEQUENCE: 37

```
cctggtatct ccgaaagcct aagggataaa cccggcgcag                            40
```

<210> SEQ ID NO 38
<211> LENGTH: 39
<212> TYPE: DNA
<213> ORGANISM: Artificial
<220> FEATURE:
<223> OTHER INFORMATION: a primer for PCR amplification of darKo

<400> SEQUENCE: 38

```
gatcgcggcc gctctcgttt tacggtattc gtccgttac                             39
```

<210> SEQ ID NO 39
<211> LENGTH: 3652
<212> TYPE: DNA
<213> ORGANISM: Artificial
<220> FEATURE:
<223> OTHER INFORMATION: a DNA fragment in which a homologous region 1
      (SEQ ID NO: 31) of darKo, bdhPp (SEQ ID NO: 21) and a homologous
      region 2 (SEQ ID NO: 36) of darKo are ligated

<400> SEQUENCE: 39

```
gccgcagacg acgtcgcaca cgccggatg caggcgatta agcatcgagg tctgcagaag       60
gaagtcgagc acctctggcg gcagcggcgc gaaaatcacc tcatccagat agcgggagat     120
tgaccgcgag ccggcgctgt gacccatcgc cgtggaggcg tccgcagaga gcgcggccat     180
tttcattccc gcgatccacc cttccgtgag cgcgattagc gcgggatcg cctgcggatc     240 cagccccgat gcgccggaga accaggcgcg ggcttcgctg ggggtaaagc gcagctcggg     300
gtcgtacacc tccagcagct gatcctgcat atgcagacgg ctgagggcta aagacggctg     360
actgcggcta ccgataatca ggtcagcgc cggcggcgca tggtccagca gccagctcat     420
tccctgatga atcgccggat cgctgatgca ttgatagtcg tcgaggatca gatacagcgg     480
gtgcgggcac tgattaagct gattaacgag ttcagcaaag aacaggggga ggtcggccgg     540
```

```
aagctcgcct tgcagcagct gcagaaacga cgggctccac ccctgccaca agggccgcag      600
cgcctcctgc agatagcgta taaacagtag cggcgcgttg tcatcctctt caaggctcag      660
ccaggccagc gcatcccctt gtcgaaggcg gtgtcgatac cactgcgcca gcagggtggt      720
tttgccaaat ccggcgggcg cgcgcaccag ggttaaacgg cgggagacgg cggcgtcgag      780
gcgctgtagc aggcgctccc gcgatagcag actttccggc gtacggggcg gcgtaaagcg      840
cgtggagata agcggcagcg tccccgtgaa gcgtaaggt tcctgatgaa caagcgctgc       900
cagcgcatca tccgccgagg ataaaaaggc cataccacga ttactcctta atccagtccg      960
tacgctcatt atcccccca tcagggggt aggccacgct tatcgcgccc gatagagtag      1020
tgccattcgc cgcagcggct acgacgacat cggccgcggg cctccctagt ttattaatca     1080
gtacaaggtg agtacagaca tgcaagcatt gagatggcat ggagtaaaag atttacgttt     1140
ggaaaacatt gagcaacccg ctgctcttcc aggaaaagta aaaatcaaag tagaatggtg     1200
tggcatttgc ggaagtgatc ttcacgaata tgtagcagga ccgatcttca ttcctgaaaa     1260
cgctcagcat ccactgactg gcgaaaaagc tccgattgtg atgggacatg aattttctgg     1320
acaagtcgtt gaaatcggtg aaggtgtaac taaaattcag gttggcgacc gtgtagtcgt     1380
agaaccggtt tttgcatgtg gagaatgtga tgcatgtaga caaggcaaat ataacctttg     1440
cgataaaatg ggcttcctcg gtttggcagg cggcggcggt ggattttctg aatatgtcgc     1500
agctgacgag cacatggttc acaaaattcc agaaagcgta tccttcgagc aaggcgcttt     1560
ggtagagcct tcggccgttg ctttgtacgc tgtacgtcaa agccaactga agtcggcga     1620 caaagctgtc gtgtttggcg ctggtcctat cggattgctg gttattgaag cgttgaaagc     1680
ttcgggcgca tctgagattt atgcagtaga gctttccgag gagcgtaaag ctaaagctga     1740
agagctgggt gctattgtgc ttgatcctaa aacttatgat gttgtggaag aactgcacaa     1800
acggaccaac ggtggcgtag atgtagccta tgaagtcact ggagtacctc ctgtgctgac     1860
tcaagcgatt gaatccacta aaattagcgg acaaatcatg atcgtcagca ttttttgaaaa    1920 agaagctcca atcaaaccga acaatatcgt tatgaaggaa cgcaatctga ctggtattat     1980
cggctaccgt gatgtattcc cggctgtcat cagcttgatg gaaaaagggt atttccctgc     2040
tgacaagctt gtgaccaaac gtattaagct cgaagaagta atcgagcaag ttttgaagg      2100 tctcctgaaa gaaaaaaatc aggttaaaat cctggtatct ccgaaagcct aagggataaa     2160
cccggcgcag aacgcgccgg ttttttgcgg ggttacgcgt tagccgcggg ctcctgcggc     2220
ttgtcgctac gggtgttttc cagcatccgg cgaaccggaa caatcagcag gcacagcacc     2280
gcggcgcaga tcagcagcgc aatagagcag cgtgcgaaca ggtcgggcag catatccagc     2340
tgatcggcct tcacgtgacc gccaatcaga cccgccgcca ggttcccag gcgctggcg     2400 cagaaccaca gccccatcat ctggccgcgc attctttccg gcgccagcag cgtcatggtc     2460
gcgaggccaa tcgggctgag gcacagctcg cccagcgtca gcatcagaat actgcccacc     2520
agccacatcg gcgagacgcc cgcgccgttg ttgctcagga cgttttgcgc cgccagcatc     2580
atcaggccaa agcccgccgc cgcgcataaa ataccgataa caaacttggt gatgctgctc     2640
ggacgcacgt ttttacgcgc cagcgcaggc cacgcccagc taaataccgg cgccagcaga     2700
ataataaaca gggcgttaat cgactggaac cacaccgccg ggatctcgaa ggagccgagc     2760
atacggttgg tatagtcgtt agcgaacagg ttaaacgagg tcggtttctg ctcaaacgcc     2820
gaccagaaaa aggcggcaga gatcagcagg ataaagcata ccagcaggcg ggcgcgctct     2880
ttgcggctca atccggcgaa gacgaacagg tagataaaat agagtaccac cgacgccgca    2940
```

```
atcacgtaga ccagtacgct ggcgaccgcc accgggttaa tcacgataac gccctgggca    3000
atcaaggcga tgataaccgc cacgcccacc gttagcgcca gcaaccatgc gccgacgcca    3060
tttcgtttca ctaccgggct gttccaggtg gaatcgaggc cgacttcact gtcgtagcgt    3120
ttcatcgccg ggacggcaaa aacgcggaag ataatcagcg cgaccagcat cccgatgccg    3180
ccgatgccga agcccagtg ccagccgtgg gatttaatca gccagccgga gatcagcggg     3240
gcgataaacg accccatgtt gatgcccata taaaacagcg agaagccgcc atcgcggcgc    3300
gcatcgcctt ttttgtagag ggtaccgacc atcaccgaaa tacaggtttt aaacaggccg    3360
gaaccgagca cgataaacat caggccaata aagaacaggc tatcgcccat caccgccgac    3420
agggcgatgg agagatggcc cagagcgatc agtatcgaac cgtaccagac cgccttttgt    3480
tgcccgagcc agttatcagc cagccagccg cccggcagcg cggcaagata catggtcccg    3540
gcaaagatcc cgacaatggc cgacgcgttc tcgcgcgcca gccccatccc accgtcatag    3600
acggtggccg ccataaacag gatcagtaac ggacgaatac cgtaaaacga ga            3652
```